(12) United States Patent
Boyanov et al.

(10) Patent No.: US 11,898,983 B2
(45) Date of Patent: Feb. 13, 2024

(54) DEVICES WITH FIELD EFFECT TRANSISTORS

(71) Applicant: Illumina, Inc., San Diego, CA (US)

(72) Inventors: Boyan Boyanov, San Diego, CA (US);
Rico Otto, San Diego, CA (US);
Jeffrey G. Mandell, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 18/003,493

(22) PCT Filed: Jun. 18, 2021

(86) PCT No.: PCT/US2021/038125
§ 371 (c)(1),
(2) Date: Dec. 27, 2022

(87) PCT Pub. No.: WO2022/005780
PCT Pub. Date: Jan. 6, 2022

(65) Prior Publication Data
US 2023/0184711 A1    Jun. 15, 2023

Related U.S. Application Data

(60) Provisional application No. 63/200,868, filed on Mar. 31, 2021, provisional application No. 63/047,743, filed on Jul. 2, 2020.

(51) Int. Cl.
*G01N 27/414* (2006.01)
(52) U.S. Cl.
CPC .............................. *G01N 27/4146* (2013.01)

(58) Field of Classification Search
CPC .................................................. G01N 27/4146
See application file for complete search history.

(56) References Cited

U.S. PATENT DOCUMENTS

| | | | |
|---|---|---|---|
| 4,057,823 A | 11/1977 | Burkhardt et al. | |
| 6,300,198 B1 | 10/2001 | Aeugle et al. | |
| 6,413,792 B1 | 7/2002 | Sauer et al. | |

(Continued)

FOREIGN PATENT DOCUMENTS

| | | |
|---|---|---|
| EP | 2 411 536 B1 | 9/2014 |
| WO | WO 11/162582 | 12/2011 |

(Continued)

OTHER PUBLICATIONS

Jiang et al., 2015, High-performance ultralow dielectric constant carbon-bridged mesoporous organosilica films for advanced interconnects, Journal of Materials Chemistry C., doi:10.1039/x0xx00000x, 8 pp.

(Continued)

*Primary Examiner* — Erik Kielin
(74) *Attorney, Agent, or Firm* — Knobbe, Martens, Olson & Bear, LLP

(57) ABSTRACT

Devices and methods of using the devices are disclosed which can provide scalability, improved sensitivity and reduced noise for sequencing polynucleotide. Examples of the devices include a biological or solid-state nanopore, a field effect transistor (FET) sensor with improved gate controllability over the channel, and a porous structure.

28 Claims, 16 Drawing Sheets

(56) References Cited

U.S. PATENT DOCUMENTS

| | | |
|---|---|---|
| 7,279,337 B2 | 10/2007 | Zhu |
| 8,079,248 B2 | 12/2011 | Hoofman et al. |
| 8,628,919 B2 | 1/2014 | Xiao et al. |
| 8,669,124 B2 | 3/2014 | Merz |
| 8,698,481 B2 | 4/2014 | Lieber et al. |
| 8,961,763 B2 | 2/2015 | Dunbar et al. |
| 9,017,937 B1 | 4/2015 | Turner et al. |
| 9,696,277 B2 | 7/2017 | Dunbar et al. |
| 9,732,381 B2 | 8/2017 | Stoddart et al. |
| 9,863,912 B2 | 1/2018 | Dunbar et al. |
| RE47,067 E | 10/2018 | Turner et al. |
| 10,096,658 B2 | 10/2018 | Watabe et al. |
| 10,135,015 B1 | 11/2018 | Doris |
| 10,297,664 B2 | 5/2019 | Xie |
| 10,324,060 B2 | 6/2019 | Lee |
| 10,366,931 B2 | 7/2019 | Xie et al. |
| 10,376,188 B2 | 8/2019 | Simpson et al. |
| 10,446,664 B1 | 10/2019 | Cheng et al. |
| 10,488,394 B2 | 11/2019 | Liu et al. |
| 10,593,780 B2 | 3/2020 | Cai et al. |
| 10,612,146 B2 | 4/2020 | Ono et al. |
| 10,629,743 B2 | 4/2020 | Cai et al. |
| 10,975,428 B2 | 4/2021 | Jayasinghe et al. |
| 11,054,390 B2 | 7/2021 | Dunbar et al. |
| 2011/0133255 A1 | 6/2011 | Merz |
| 2012/0000274 A1 | 1/2012 | Fife |
| 2014/0190824 A1 | 7/2014 | Credo et al. |
| 2015/0014752 A1* | 1/2015 | D'Emic ............. G01N 27/4146 257/253 |
| 2016/0231307 A1* | 8/2016 | Xie .................... B01L 3/50273 |
| 2019/0120830 A1 | 4/2019 | Hoffman |
| 2020/0292521 A1 | 9/2020 | Xie et al. |
| 2021/0147486 A1 | 5/2021 | Remaut et al. |

FOREIGN PATENT DOCUMENTS

| | | |
|---|---|---|
| WO | WO 13/171144 | 11/2013 |
| WO | WO 19/160925 | 8/2019 |

OTHER PUBLICATIONS

Kleeman et al., 2020, A review of vertical organic transistors, Advanced Functional Materials, 30:1907113.

Loubet et al., 2017, Stacked nanosheet gate-all-around transistor to enable scaling beyond finFET, Symposium on VLSA Technology Digest of Technical Papers, pp. T230-T231.

Pai et al., Jan. 23, 2005, Mesoporous silicates prepared using preorganized templates in supercritical fluids, Science, 303:507-510.

Saraswat, Thin dielectrics for MOS gate, EE 311 Notes, Handout #3, 46 pp.

International Search Report and Written Opinion dated Nov. 16, 2021, in application No. PCT/US2021/038125.

* cited by examiner

DEVICES WITH FIELD EFFECT TRANSISTORS

CROSS-REFERENCE TO RELATED APPLICATIONS

This application is a U.S. national phase application under 35 U.S.C. § 371 of International Application No. PCT/US2021/038125, filed Jun. 18, 2021, which claims priority to U.S. Provisional Application No. 63/047,743, filed Jul. 2, 2020, and U.S. Provisional Application No. 63/200,868, filed Mar. 31, 2021, the content of each of which is incorporated by reference in its entirety.

BACKGROUND

Various polynucleotide sequencing techniques involve performing a large number of controlled reactions on support surfaces or within predefined reaction chambers. The controlled reactions may then be observed or detected, and subsequent analysis may help identify properties of the polynucleotide involved in the reaction.

Some of these polynucleotide sequencing techniques utilize a nanopore, which can provide a path for an ionic electrical current. For example, as the polynucleotide traverses through the nanopore, it influences the electrical current through the nanopore. Each passing nucleotide, or series of nucleotides, that passes through the nanopore yields a characteristic electrical current. These characteristic electrical currents of the traversing polynucleotide can be recorded to determine the sequence of the polynucleotide.

FIG. 1A shows a prior art nanopore sequencing device 1110 as shown in PCT publication WO 2019/160925. The prior art nanopore sequencing device 1110 includes a cis well 1114 associated with a cis electrode 1130, a trans well 1116 associated with a trans electrode 1134, and a field effect transistor (FET) 1122 positioned between the cis well 1114 and the trans well 1116. The FET 1122 includes a source 1150, a drain 1152, and a channel 1154. Below the cis well 1114 is a first cavity 1115 facing the cis well 1114. The trans well 1116 includes a second cavity 1117. A fluidic tunnel 1121 extends through the FET 1122 from the first cavity 1115 to the trans well 1116. An electrolyte 1120 is disposed in the cis well 1114, first cavity 1115 and trans well 1116.

Between the cis well 1114 and first cavity 1115 is a nanopore 1118 that is disposed into a membrane 1124. The nanopore 1118 has first nanoscale opening 1123 fluidically and electrically connecting electrolyte from the cis well 14 to the first cavity 1115. The first nanoscale opening 1123 has an inner diameter 1123'. As the polynucleotide 1129 traverses through the first nanoscale opening 1123, the sequence of the polynucleotide can be determined by measuring the change in voltage of the FET sensor 1122. A second nanoscale opening 1125 within a base substrate 1162' fluidically connects the fluidic tunnel 1121 and the second cavity 1117, with the second nanoscale opening 1125 having an inner diameter 1125'.

Metallic interconnects 1164' and 1166' are in electrical communication with the source 1150 and drain 1152 of the FET 1122. A relatively thick interlayer dielectric 1168, generally thicker than about 50 nm, surrounds the channel 1154 and upper and lower surfaces of the FET sensor 1122 to form the fluidic tunnel 1121. The FET sensor 1122 is in electrical communication with the electrolyte 1120 at the boundary 1156 where the channel 1154 is closest to the fluidic tunnel 1121. As illustrated, the thickness of the interlayer dielectric 1168 on top of, or below, the channel 1154 may be about 3 times or more the thickness of the channel 1154 of the FET 1122.

SUMMARY

Provided in examples herein are devices for sequencing polynucleotides and methods of using the devices. One example of such a device is a nanopore device. In particular, examples include devices having a field effect transistor (FET) sensor and a porous structure.

The systems, devices, kits, and methods disclosed herein each have several aspects, no single one of which is solely responsible for their desirable attributes. Without limiting the scope of the claims, some prominent features will now be discussed briefly. Numerous other examples are also contemplated, including examples that have fewer, additional, and/or different components, steps, features, objects, benefits, and advantages. The components, aspects, and steps may also be arranged and ordered differently. After considering this discussion, and particularly after reading the section entitled "Detailed Description," one will understand how the features of the devices and methods disclosed herein provide advantages over other known devices and methods.

One example is a device comprising a middle well comprising a fluidic tunnel; a cis well associated with a cis electrode, wherein a first nanoscale opening is disposed between the cis well and the middle well; a trans well associated with a trans electrode, wherein a second nanoscale opening is disposed between the trans well and the middle well; and a field effect transistor (FET) positioned between the first nanoscale opening and the second nanoscale opening. In this example, the FET comprises: a source, a drain, and a channel connecting the source to the drain, wherein the channel comprises a gate oxide layer having an upper surface fluidically exposed to the middle well, wherein the middle well fluidically connects the cis well to the trans well. In some embodiments, the fluidic tunnel extends through the channel. In alternative embodiments, the fluidic tunnel is offset from (i.e., does not extend through) the FET channel.

Another example is a device comprising a middle well comprising a fluidic tunnel; a cis well associated with a cis electrode, wherein a first nanoscale opening is disposed between the cis well and the middle well; a trans well associated with a trans electrode, wherein a second nanoscale opening is disposed between the trans well and the middle well; and a field effect transistor (FET) positioned between the first nanoscale opening and the second nanoscale opening, the FET comprising: a source, a drain, and a channel connecting the source to the drain, wherein the channel comprises a gate oxide layer having an upper surface and a lower surface, the surfaces fluidically exposed to the middle well, wherein the middle well fluidically connects the cis well to the trans well. In some embodiments, the fluidic tunnel extends through the channel. In alternative embodiments, the fluidic tunnel is offset from (i.e., does not extend through) the FET channel.

Yet another example is a device comprising a middle well comprising a fluidic tunnel; a cis well associated with a cis electrode, wherein a first nanoscale opening is disposed between the cis well and the middle well; a trans well associated with a trans electrode, wherein a porous structure is disposed between the trans well and the middle well; and a field effect transistor (FET) positioned between the first nanoscale opening and the porous structure, the FET comprising: a source, a drain, and a channel connecting the source to the drain, wherein the channel comprises a gate oxide layer having an upper surface fluidically exposed to the middle well, wherein the middle well fluidically connects the cis well to the trans well. In some embodiments, the fluidic tunnel extends through the FET channel. In alternative embodiments, the fluidic tunnel is offset from (i.e., does not extend through) the FET channel.

Still another example is a method of using the any of the aforementioned devices in method comprising: introducing an electrolyte into each of the cis well, the trans well, the middle well and the fluidic tunnel of a device, applying a voltage bias between the cis electrode and the trans electrode, wherein an electrical resistance of the first nanoscale opening varies in response to an identity of bases in the polynucleotide at the first nanoscale opening, and wherein a potential ($V_M$) of the electrolyte in the fluidic tunnel varies in response to the variation in electrical resistance of the first nanoscale opening; and measuring a response of the FET as a function of bases in the polynucleotide at the first nanoscale opening, to identify the bases in the polynucleotide.

It is to be understood that any features of the device and/or of the array disclosed herein may be combined together in any desirable manner and/or configuration. Further, it is to be understood that any features of the method of using the device may be combined together in any desirable manner. Moreover, it is to be understood that any combination of features of this method and/or of the device and/or of the array may be used together, and/or may be combined with any of the examples disclosed herein. Still further, it is to be understood that any feature or combination of features of any of the devices and/or of the arrays and/or of any of the methods may be combined together in any desirable manner, and/or may be combined with any of the examples disclosed herein.

It should be appreciated that all combinations of the foregoing concepts and additional concepts discussed in greater detail below are contemplated as being part of the inventive subject matter disclosed herein and may be used to achieve the benefits and advantages described herein.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

All patents, applications, published applications and other publications referred to herein are incorporated herein by reference to the referenced material and in their entireties. If a term or phrase is used herein in a way that is contrary to or otherwise inconsistent with a definition set forth in the patents, applications, published applications and other publications that are herein incorporated by reference, the use herein prevails over the definition that is incorporated herein by reference.

One example relates to a sequencing device that includes a field effect transistor (FET) sensor having channel disposed between the source and the drain of the FET sensor. While in many instances herein, the sequencing device are described as nanopore devices, the devices need not be nanopore devices and other configurations are possible. In one example, the channel has an upper surface, a lower surface, or both exposed to electrolyte within the device. The exposed upper and/or lower surface of the FET sensor provides an increased surface area of the FET in electrical contact with the electrolyte that improves the sensitivity of the nanopore sequencing device. Moreover, increasing the surface area of the FET exposed to the electrolyte was found to reduce the background electrical noise in the sensor, thus providing a multi-factor boost to the signal-to-noise ratio (SNR) when measuring nucleic acid sequences that come in contact with the nanopore.

Figure 4A:
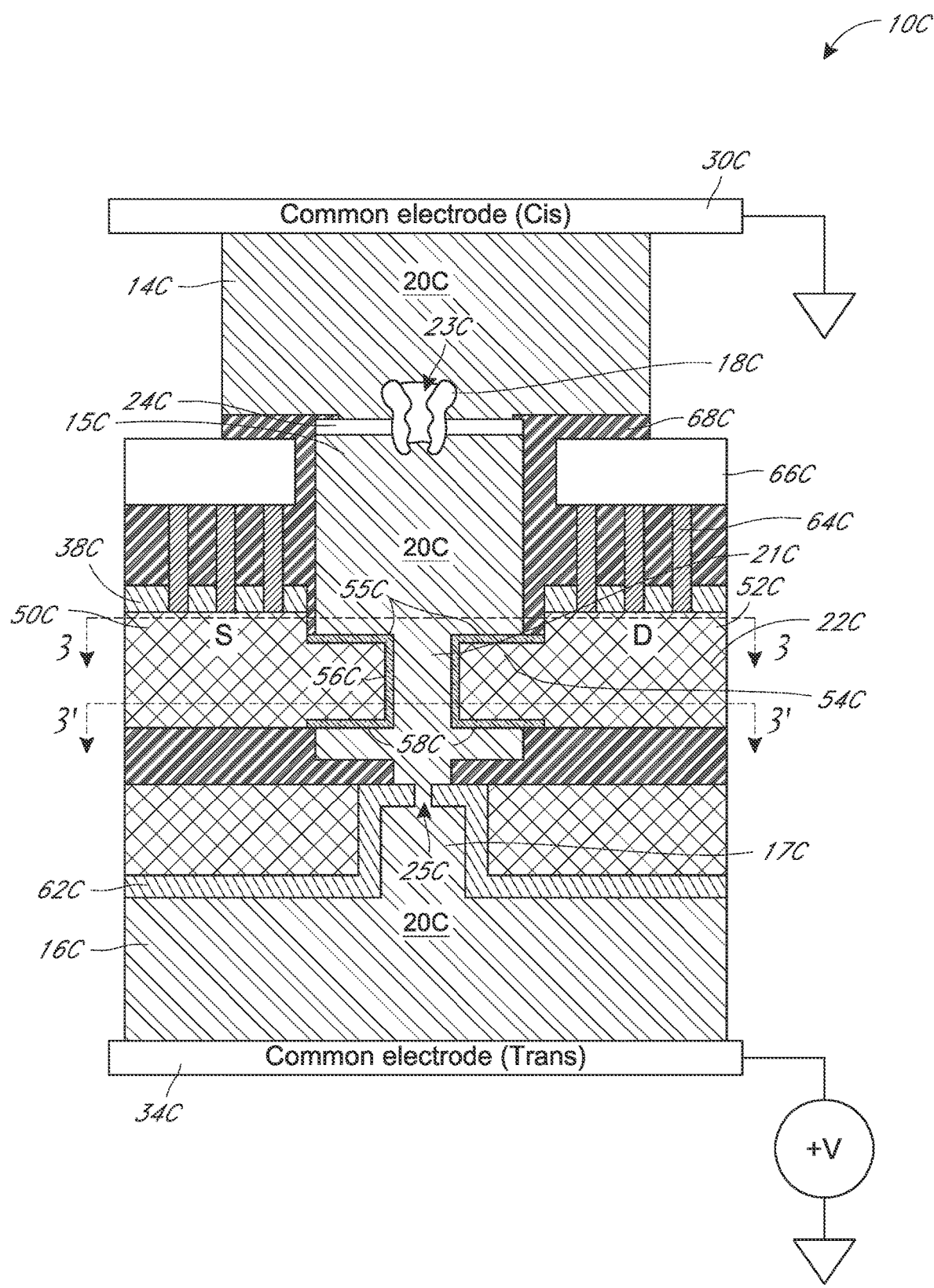
FIG. 4A is another cross-sectional side view of an alternate example of a nanopore sequencing device.
Figure 4B:
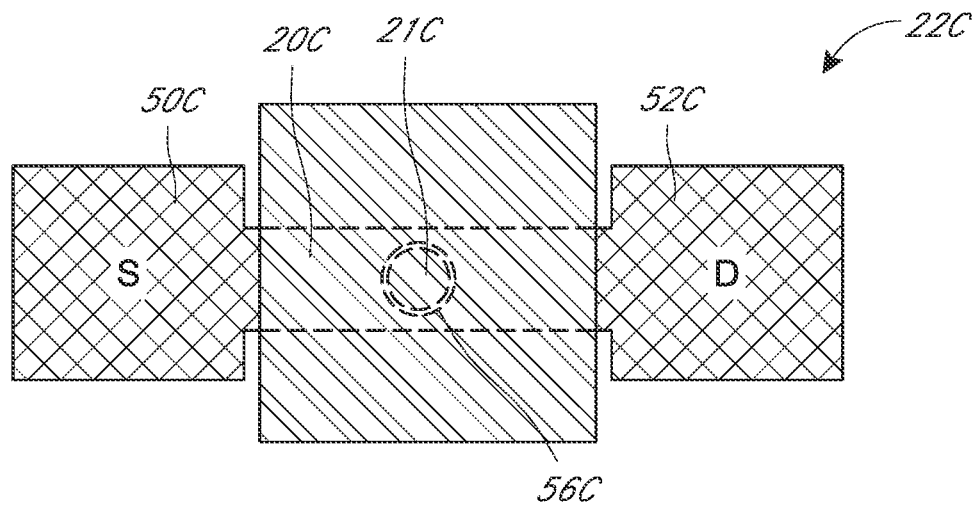
FIG. 4B is a cross-sectional top view, taken on line 3-3 of the nanopore sequencing device of FIG. 4A.
Figure 4B:
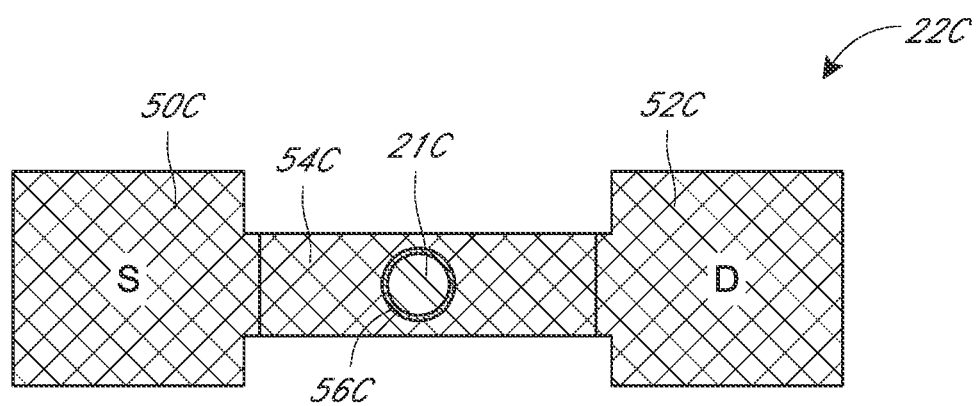
Figure 6:
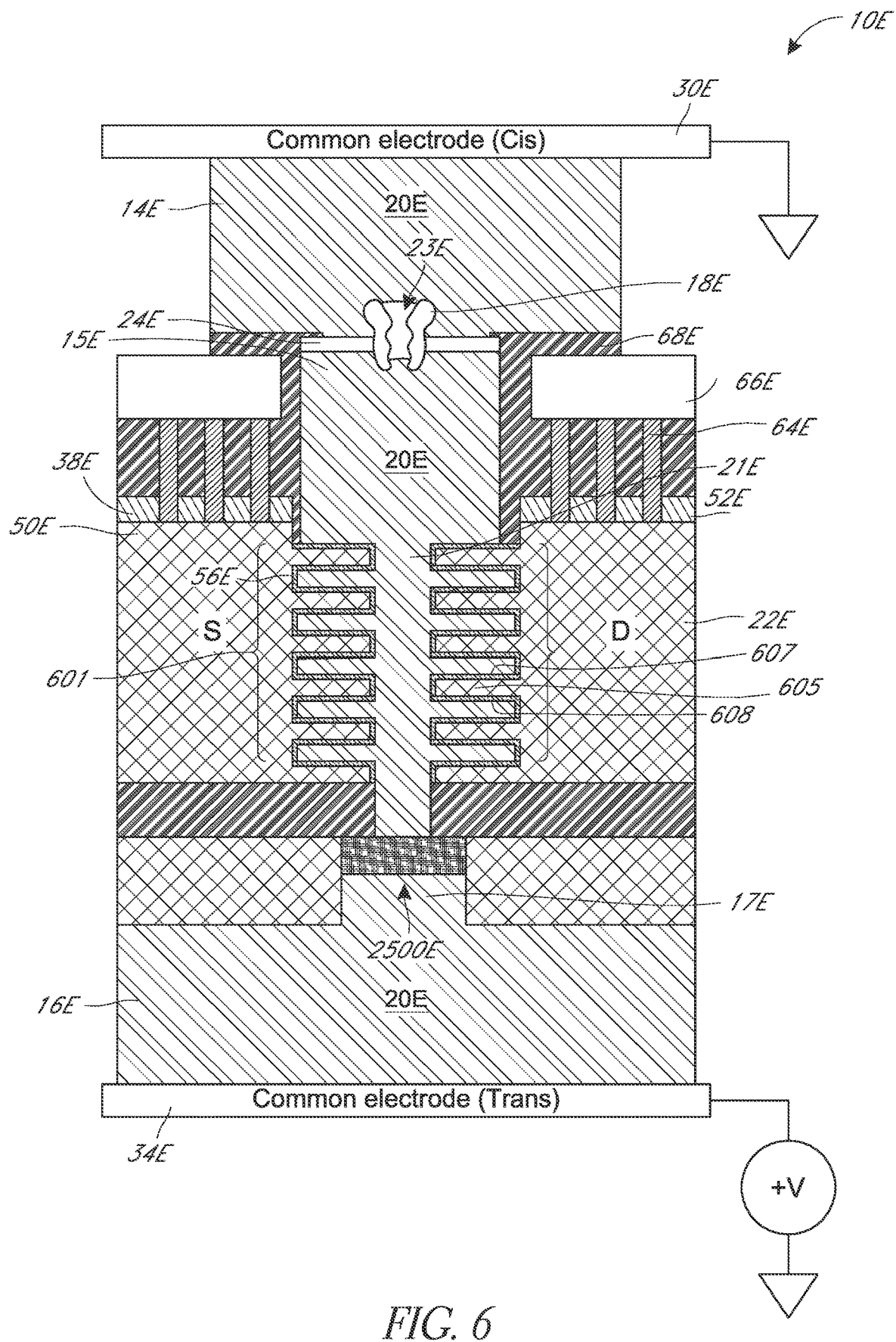
FIG. 6 is a cross-sectional side view of another exemplary alternate example of a nanopore sequencing device.
Figure 8:
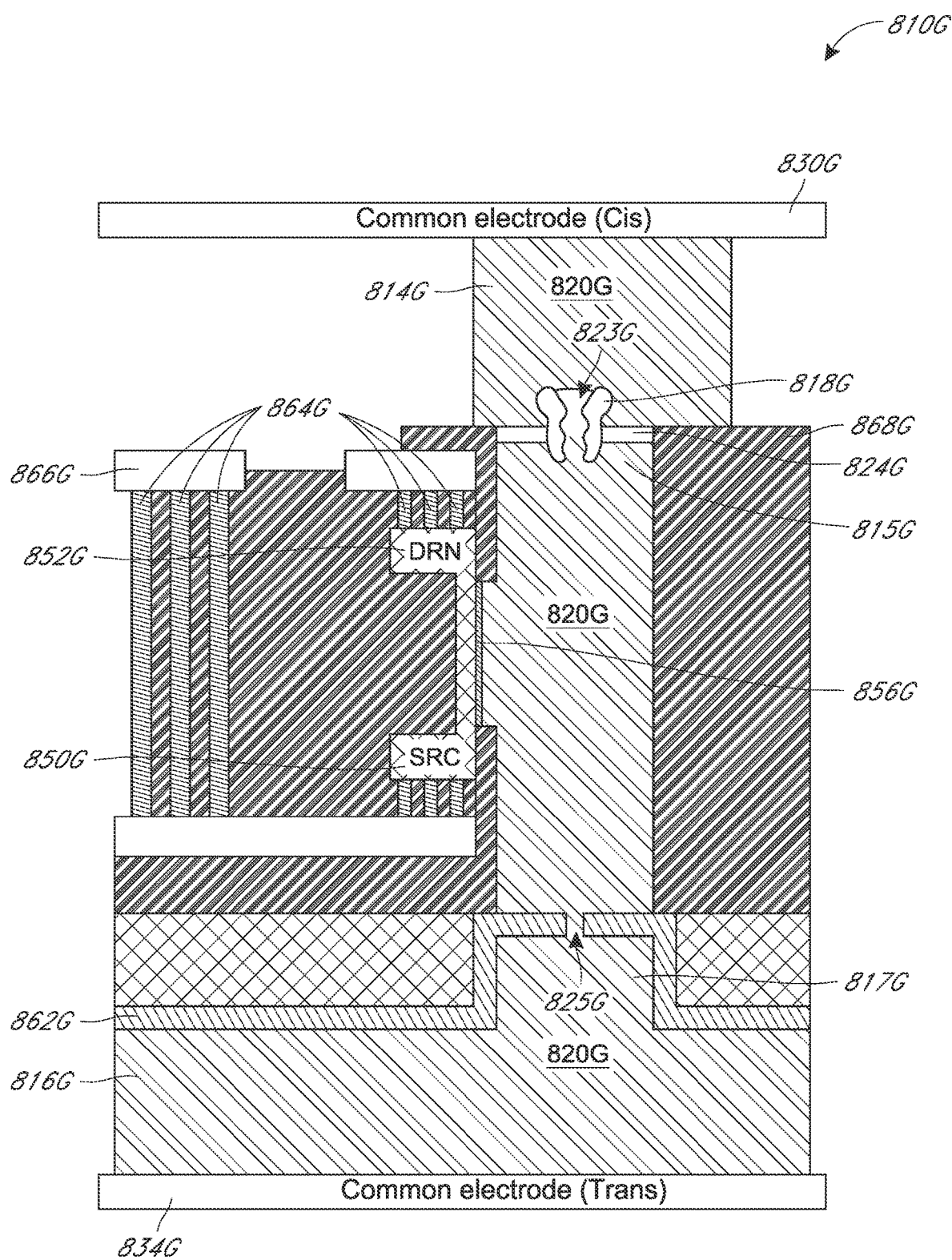
FIG. 8 is a cross-sectional side view of a further exemplary alternate example of a nanopore sequencing device with a vertical field effect transistor.

In one example, the nanopore sequencing system utilizes an FET sensor built with gate-all-around (GAA) transistors to further increase the signal to noise ratio of the device. This GAA technology allows the FET sensor to not only have an upper surface that is exposed to electrolyte, but also have a lower surface that is also exposed to electrolyte. More information regarding this structure is described below with reference to FIG. 4A. In one embodiment, one or more gate-all-around transistors of the nanopore sequencing system may comprise an upper surface and a lower surface of the source-drain channel exposed to an electrolyte as shown in FIGS. 4A, 4B and 4B'. In another embodiment, one or more gate-all-around transistors of the nanopore sequencing system may comprise an upper surface and a lower surface of a plurality of source-drain channels exposed to an electrolyte as shown in FIG. 6. In yet another embodiment, one or more gate-all-around transistors of the nanopore sequencing system may comprise vertical transistors as shown in FIG. 8.

Figure 9:
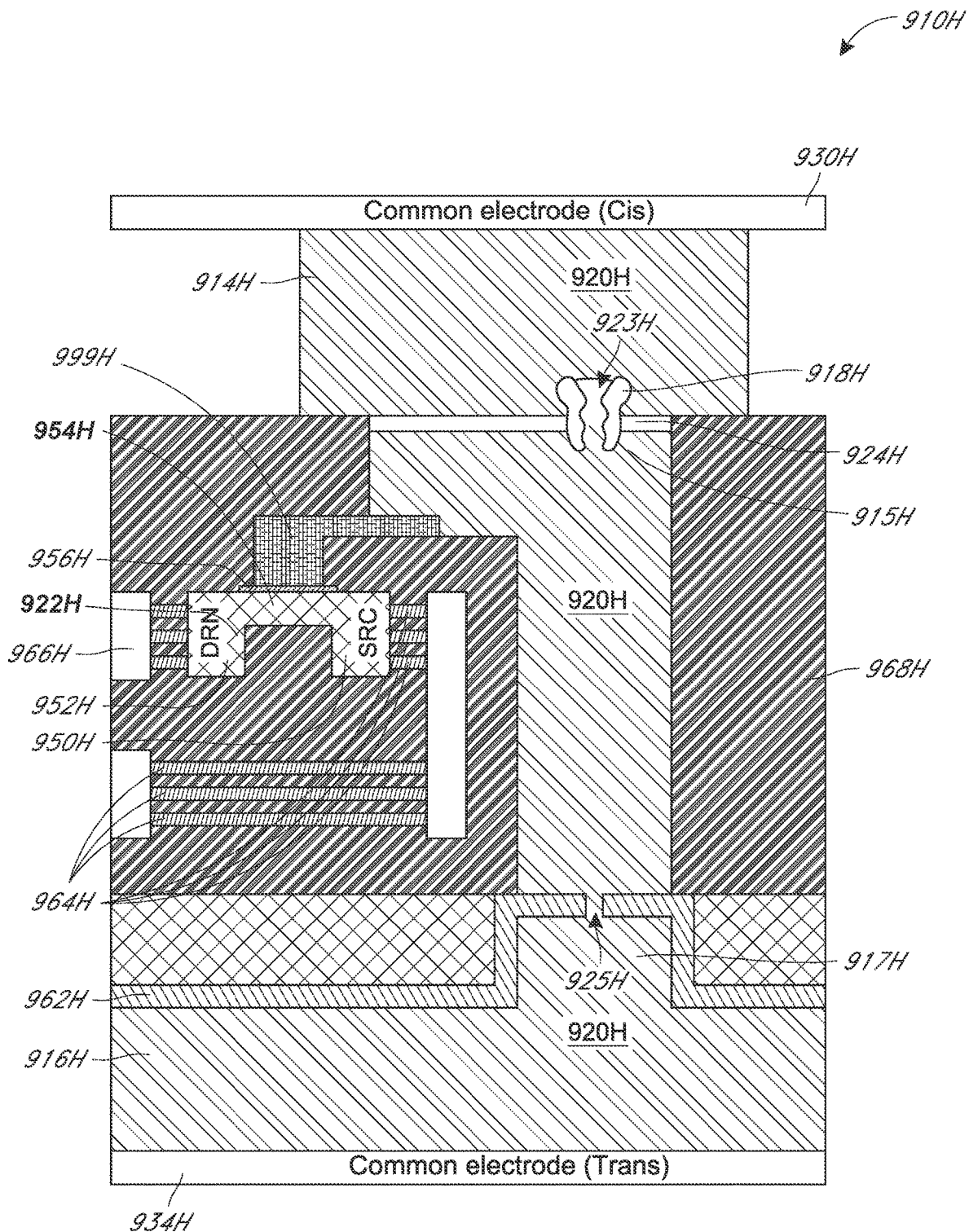
FIG. 9 is a cross-sectional side view of yet another further exemplary alternate example of a nanopore sequencing device with a field effect transistor having a non-Faradaic metal electrode.

In another example, the FET is not in direct contact with the electrolyte. Instead, a non-Faradaic metal electrode as shown in FIG. 9 is exposed to the electrolyte and transmits a detected signal to the sensing FET. This configuration allows for a significant simplification of the fabrication process and a better compatibility with conventional semiconductor process flows.

In another example, the solid-state nanopore structure may be replaced with a porous structure, as discussed in more detail below. Such porous structures may be more readily integrated into a semiconductor fabrication process flow.

As used herein, the term "exposed to electrolyte" does not necessarily mean that a component is directly contacting the electrolyte. For example, a FET sensor or a channel of a FET sensor that is exposed to electrolyte may comprise a relatively thin layer of an insulator between the sensor or channel and the electrolyte. For example, in one example the channel portion of the FET sensor located between the source and drain may be covered by a relatively thin layer of a gate oxide, for example a thermally grown silicon dioxide layer, and the channel with its gate oxide is said to be "exposed to electrolyte". Alternatively, a thin layer of an insulator may be formed of high-k dielectrics, such as $HfO_2$, $Al_2O_3$, silicon nitroxides, $Si_3N_4$, $TiO_2$, $Ta_2O_5$, $Y_2O_3$, $La_2O_3$, $ZrO_2$, $ZrSiO_4$, barium strontium titanate, lead zirconate titanate, $ZrSi_xO_y$, or $ZrAl_xO_y$. The layer of gate oxide may be about 10 nm in thickness, or in other examples, less than about 9, about 8, about 7, about 6, about 5, about 4, about 3, about 2, or about 1 nm in thickness and still be within examples described herein.

Electrical Operation of a Nanopore Sequencing Device

Figure 1A:
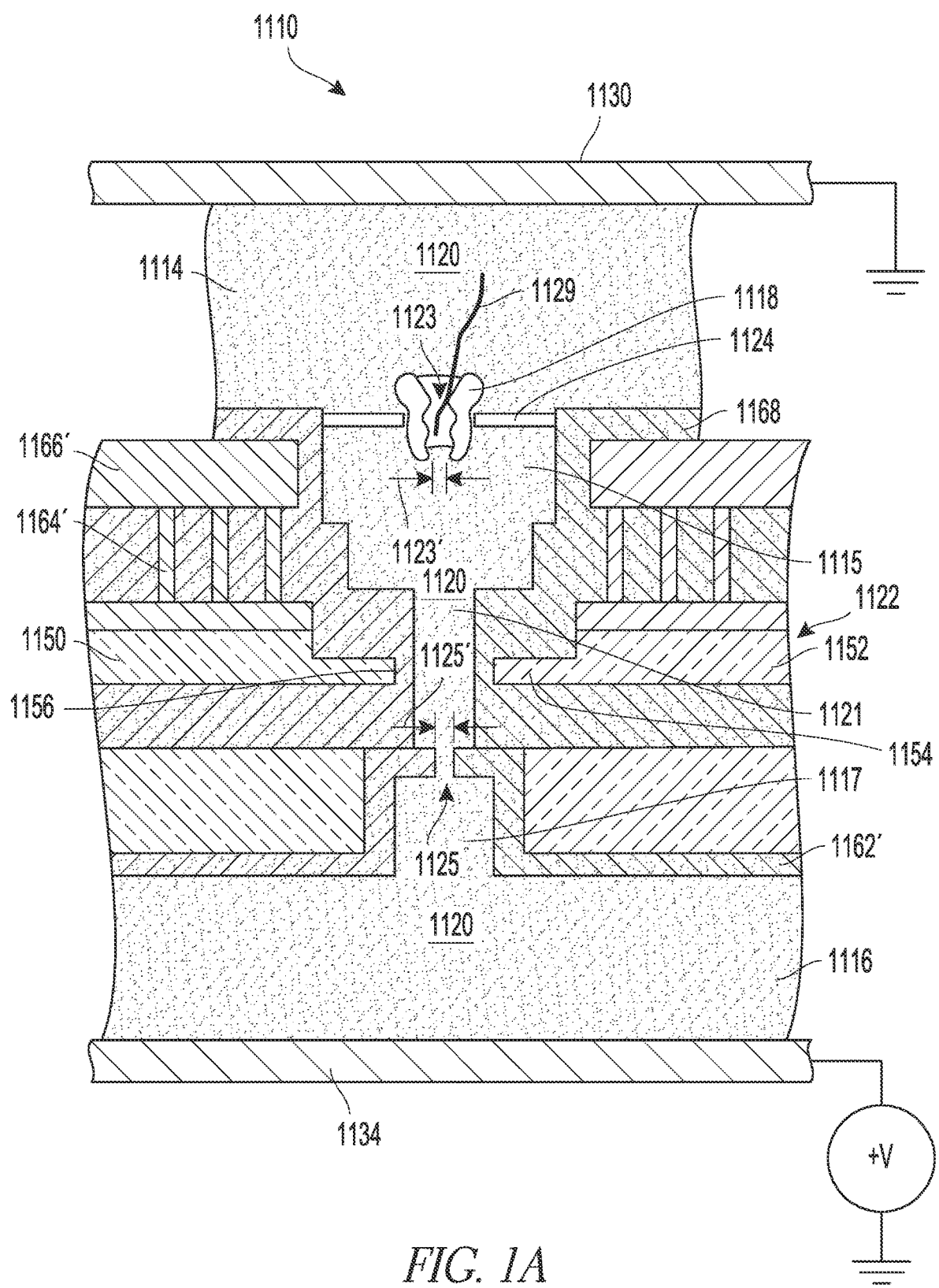
FIG. 1A is a cross-sectional side view of a prior art nanopore sequencing device.
Figure 1B:
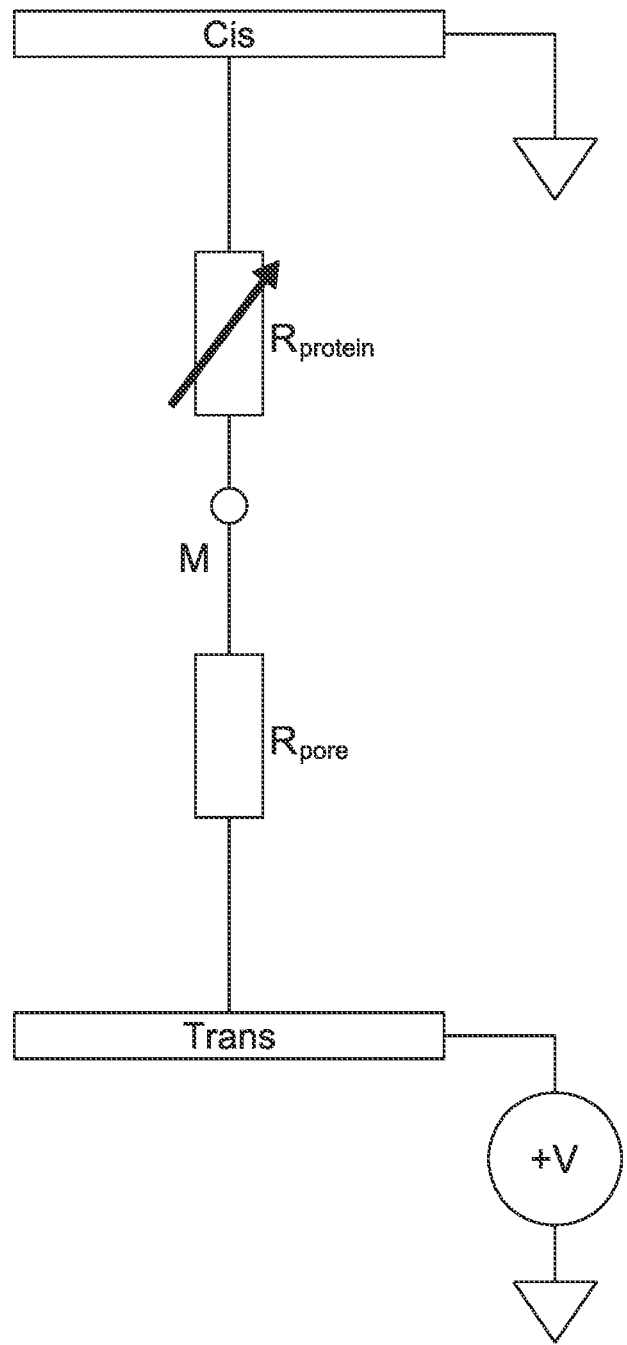
FIG. 1B shows a schematic circuit diagram of the electrical resistance provided by the prior art nanopore sequencing device of FIG. 1A.

Referring now to FIG. 1B, an equivalent circuit diagram of a nanopore device, such as a nanopore device illustrated in FIGS. 2-7, is shown. As electrolyte is introduced into each of the cis well, the trans well, the middle well, and the fluidic tunnel. A voltage difference V is applied between the cis electrode and the trans electrode. In some examples, a polynucleotide is driven through a first nanoscale opening of a first nanopore, e.g. a protein nanopore. In alternative examples, the polynucleotide does not pass through the first nanopore, but tagged nucleotides are incorporated by a polymerase acting on the polynucleotide. In certain embodiments, a single-stranded polynucleotide, a double-stranded polynucleotide, tags or labels of incorporated nucleotide bases, or other representatives of the incorporated nucleotide bases, and any combination thereof may pass through the first nanopore. In certain embodiments, tags or labels of incorporated nucleotide base may be separated or dissociated from a polynucleotide, and such tags or labels may pass through the first nanopore with or without the polynucleotide passing through the first nanopore. Examples are not limited to how the polynucleotide communicates with the nanopore to cause signal generation in the nanopore sequencing device. An electrical resistance $R_{protein}$ of the first nanoscale opening varies in response to an identity of bases at the first nanoscale opening, e.g., while a base of the polynucleotide passes through the first nanoscale opening, or while a tagged nucleotide is being incorporated by a polymerase acting on the polynucleotide, thus the different tags of the tagged nucleotides change the resistance of the first nanoscale opening.

In an example, a second nanoscale opening of a second nanopore, e.g., a solid-state nanopore, has a fixed, or substantially fixed electrical resistance $R_{pore}$. A potential of the electrolyte in the fluidic tunnel, denoted as the voltage divider point M in FIG. 1C, varies in response to the variation in electrical resistance $R_{protein}$ of the first nanoscale opening. Therefore, measuring the response of the FET as the resistance changes in the first nanoscale opening permits determination of the resistance in the first nanoscale opening, and such information can be used to identify the base in the polynucleotide.

During a nanopore sequencing operation, the application of the electrical potential (i.e., voltage difference V) across the first nanopore may force the translocation of a nucleotide through the first nanoscale opening along with the anions carrying charges. Depending upon the bias, the nucleotide may be transported from the cis well to middle well, or from the middle well to the cis well. As the nucleotide transits through the first nanoscale opening, the current across the membrane 24 changes due, for example, to base-dependent blockage of the constriction, for example. The signal from that change in current can be measured using the FET sensor. Examples of measuring the response of the FET include: measuring a source drain current; or measuring a potential at the source and/or drain. Additionally, a resistance in the FET channel can be measured to identify the base at the first nanoscale opening.

During operation, the range of measured voltages can be selected from about −0.1 V to upwards of about 0.1 V, from about −0.5 V to upwards of about 0.5 V, from about −1 V to upwards of about 1 V, from about −1.5 V to upwards of about 1.5 V, from about −2.0 V to upwards of about 2.0 V, from about −3.0 V to upwards of about 3.0 V, from about −5.0 V to upwards of about 5.0 V. The voltage polarity is typically applied such that the negatively charged nucleic acid is electrophoretically driven towards the trans electrode. In some instances, the voltage can be reduced, or the polarity reversed, to facilitate appropriate function of the device. In one non-limiting example, the resistance of the first nanoscale opening, $R_{protein}$, may be about 0.5 to about 1 giga-ohm (GΩ). The resistance of the second nanoscale opening, $R_{pore}$, may be about 50 mega-ohm (MO). In one example, $R_{protein}$ changes as a function of the base of the polynucleotide at the first nanoscale opening.

The potential of the voltage divider point M varies with $R_{protein}$ and acts as the FET gate potential. The resistance $R_{pore}$ of the second nanoscale opening, which may be formed in a solid-state nanopore, is fixed or at least substantially fixed and is not modulated by the base of the polynucleotide at the first nanoscale opening. For example, as the polynucleotide enters the constriction of the first nanoscale opening, the resistance $R_{protein}$ of the first nanoscale opening is modulated based on the identity of the bases in the polynucleotide. Alternatively, the resistance $R_{protein}$ of the first nanoscale opening is modulated based on the identity of a tag of a tagged nucleotide that is being incorporated by a polymerase acting on the polynucleotide. The resistance $R_{protein}$ may be relatively large, and generally varies by 30-40% as a function of different polynucleotide bases at the first nanoscale opening. In other examples, the resistance $R_{protein}$ may vary by between about 0.001% to about 1%, about 1% to about 5%, about 5% to about 20%, about 20% to about 40%, about 40% to about 60%, or 60% to about 100%. The resistance $R_{pore}$ of the second nanoscale opening, which may be have a larger size than the first nanoscale opening, may be about 10 times lower compared to $R_{protein}$. Since the function of the second nanoscale opening is to provide the fixed resistance $R_{pore}$ in the voltage divider (but not to read out the current associated with the first nanoscale opening), the second nanoscale opening may not need to be atomically precise.

The equivalent circuit shown in FIG. 1B is a voltage divider, where the potential of point M is the potential of the electrolyte in the fluidic tunnel. This potential is the equivalent gate potential of the FET and establishes its operating point. As the potential $V_M$ of point M changes with base identity of the polynucleotide, the current flowing through the FET (the source-drain current) changes, providing a measurement of the current flowing through the first nanoscale opening, and therefore of the identity of polynucleotide base. In certain embodiments, the equivalent circuit of the nanopore device satisfies the following equations:

The potential $V_M$ at point M is given by $$V_M = DV \text{ where} \quad (1)$$

$$D = \frac{R_{protein}}{R_{pore} + R_{protein}} \quad (2)$$

is the voltage divider ratio and V is the cis-trans bias.

The signal that drives the FET sensor response is $\delta V_M$, the variation of the potential $V_M$ as the base of the polynucleotide at the first nanoscale opening changes. From the above the following relationship can be derived:

$$\delta V_M = V \delta D \quad (3)$$

where $\delta D$ is the variation in the voltage divider ratio as the base of the polynucleotide at the first nanoscale opening changes.

The signal $\delta V_M$ may exceed the limit of detection (LoD) of the FET sensor, i.e., $V \delta D > LoD$. Therefore, the sensitivity of the nanopore device 10 improves as LoD is reduced, V is increased, or $\delta D$ is increased.

The operating cis-trans bias V may therefore satisfy;

$$V > \frac{LoD}{\delta D} \quad (4)$$

Examples

Figure 2A:
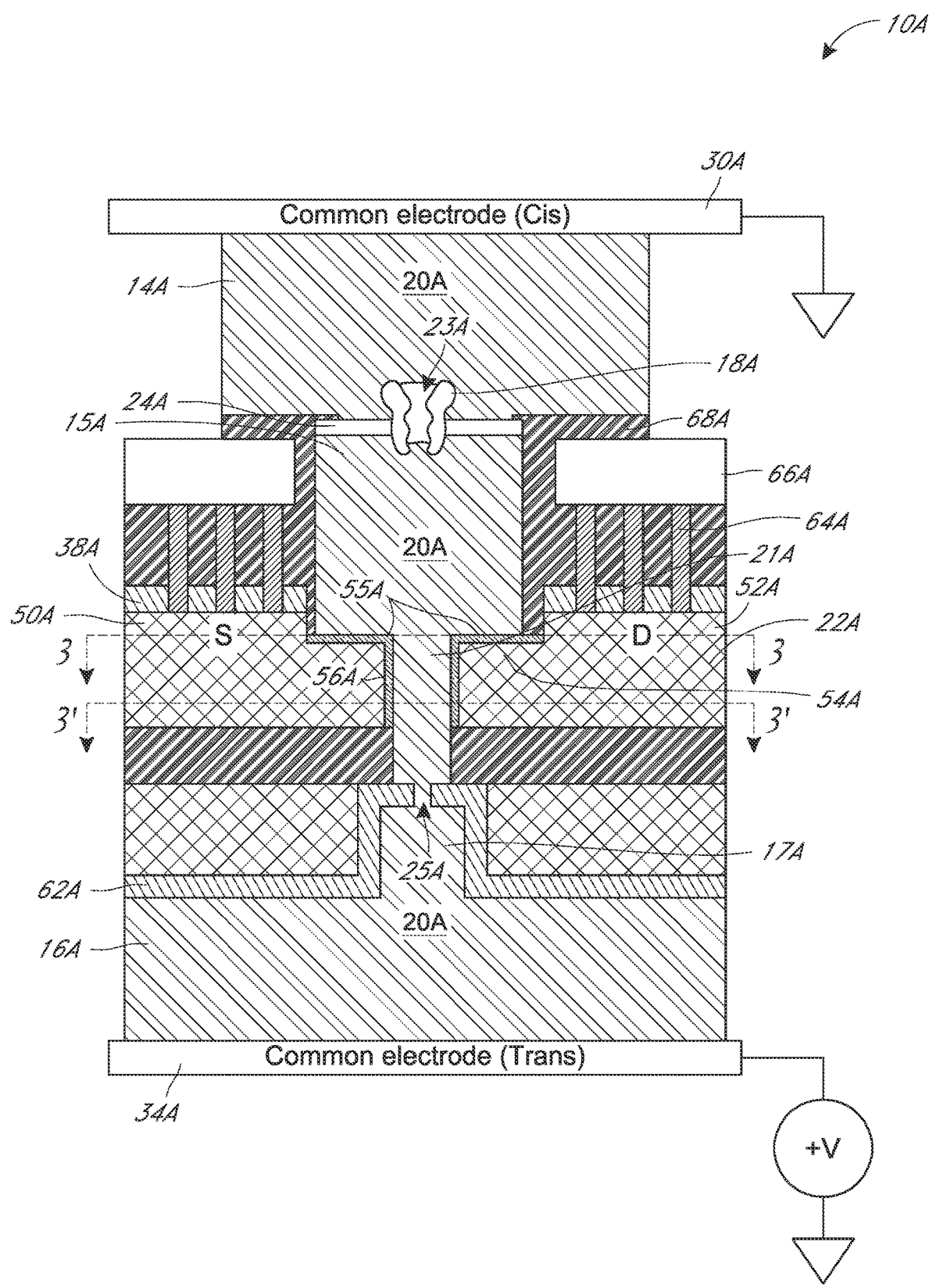
FIG. 2A is a cross-sectional side view of a nanopore sequencing device according to one example.
Figure 2B:
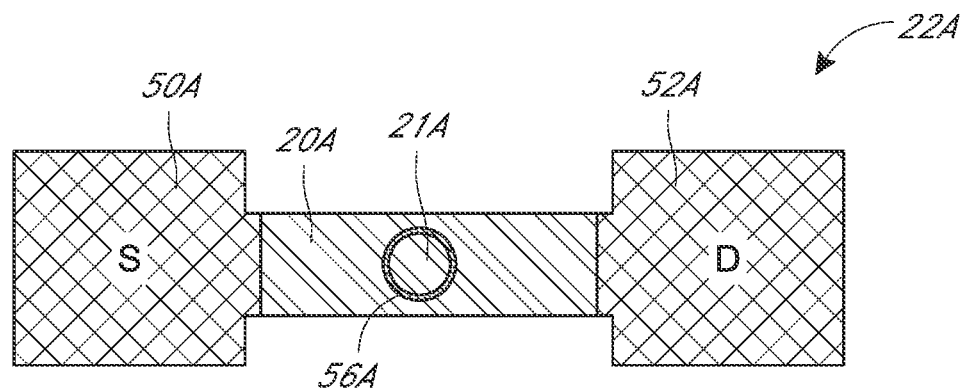
FIG. 2B is a cross-sectional top view, taken on line 3-3 of the nanopore sequencing device of FIG. 2A.
Figure 2B:
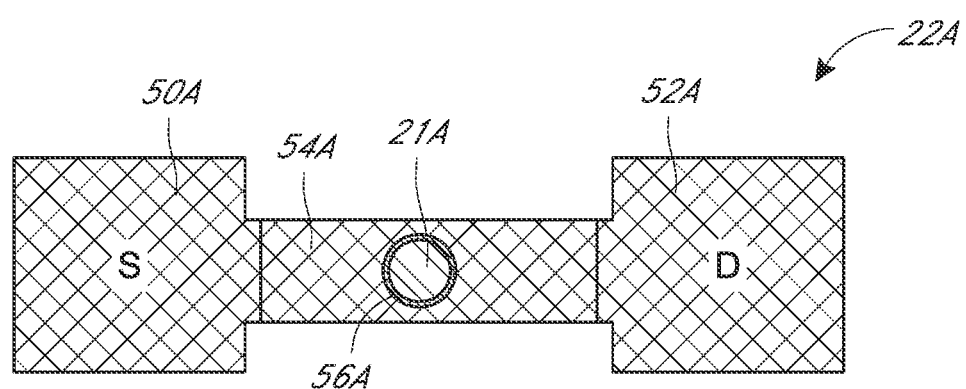

One example of a nanopore sequencing device with an FET sensor having an increased surface area exposed to electrolyte is shown in FIG. 2A. FIG. 2A is a side cross-sectional view of the exemplary device 10A. FIG. 2B is a cross-sectional top view, taken on line 3-3 of FIG. 2A. FIG. 2B' is a cross-sectional top view, taken on line 3'-3' of FIG. 2A.

The nanopore sequencing device 10A shown in FIGS. 2A, 2B, and 2B' includes a cis electrode 30A connecting to a cis well 14A. The cis well 14A has a lower portion that includes a first nanopore 18A disposed into a membrane 24A. The first nanopore 18A includes a first nanoscale opening 23A defined by the first nanopore 18A that communicates with a fluidic tunnel 21A to a second nanoscale opening 25A disposed in a narrower region 17A between the fluidic tunnel 21A and a trans well 16A at a lower portion of the device 10A. As shown, the second nanoscale opening is formed in the substrate material 62A. The first nanopore 18A provides a fluidic pathway for electrolyte 20A to pass between the cis well 14A and the middle well 15A. The fluidic tunnel 21A provides a fluidic pathway for the electrolyte to pass from the middle well 15A, through the second nanoscale opening 25A and to the trans well 16A.

In one example, the cis electrode 30A and the trans electrode 34A are at least substantially parallel to one another in an at least substantially horizontal direction. In other examples, the cis electrode and the trans electrode may be in any suitable orientation relative to each other and to the nanopore device. The nanopore device 10A further includes a field effect transistor (FET) sensor 22A positioned between the first nanoscale opening 23A and the second nanoscale opening 25A. The FET sensor includes a source (S) 50A, a drain (D) 52A, and a channel 54A that connects the source 50A to the drain 52A. As shown in top views, FIGS. 2B and 2B', the electrolyte 20A can be seen in the fluidic tunnel 21A and extending through the channel 54A. Metallic interconnects 64A and 66A are in electrical communication with the source 50A and drain 52A of the FET 22A, through the etch stop layer 38A. The metallic interconnects 64A and 66A communicate data from the FET sensor 22A to a control system monitoring the FET sensor 22A.

In the example of the nanopore device 10A shown in FIG. 2A, a thin layer of gate oxide 56A is grown around the channel 54A, therefore its upper surface 55A is fluidically exposed to the electrolyte 20A in the middle well 15A. The gate oxide 56A may have a vertical surface fluidically exposed to the electrolyte 20A in the fluidic tunnel 21A. The thin layer of gate oxide 56A separates the channel 54A from the electrolyte 20A and exposes the channel 54A of the FET sensor 22A to the electrolyte 20A. The thickness of the gate oxide 56A may be between about 1 and about 10 nm, or alternatively between about 2 and about 4 nm. The thickness of the gate oxide 56A is chosen such that a strong enough electric field, given the potential $V_M$, can induce an inversion layer of electrons, or holes, which constitute a conductive path at the boundary of the channel 54A and gate oxide 56A to provide a measurable conduction between the source 50A and drain 52A of the FET 22A.

In this configuration, the upper surface 55A of the gate oxide 56A of the channel 54A fluidically exposes the channel 54A to the electrolyte in the middle well 15A, as shown in FIG. 2B. By providing a large area of the channel 54A exposed to the electrolyte 20A, the potential $V_M$ has a better gate controllability over the channel 54A.

Following equations (2) and (4) above, assuming that the expected level separation in $R_{protein}$~10% of the open pore resistance, with an expected base divider ratio D~0.1, then the variation $\delta D$~0.1×0.1=0.01. Using a FET sensor with a 3 mV LoD implies $$V > \frac{0.003V}{0.01} = 0.3V. \quad (5)$$

Such high cis-trans bias V may be incompatible with some choices of the membrane 24A.

Reduction of the LoD to about 0.2 mV reduces the required cis-trans bias V by about 15× (15 times), to about 20 mV, which is compatible with typical membranes. This means FET sensors with large gate areas would be advantageous. In the FET sensor as shown in prior art FIG. 1A, only a small fraction of the channel 1154 is exposed to the variation in voltage $\delta V_M$, mainly through the gate oxide 56A at the boundary of the fluidic tunnel 21A. In addition to exposing the channel 54A to the variation in voltage through the boundary of the fluidic tunnel 21A, the structure with the exposed upper surface 55A as shown in FIGS. 2A, 2B and 2B' greatly increases the sensing area of the FET exposed to $\delta V_M$ and improves the LoD, which scales as 1/sqrt(A), where A is the area of the channel 54A exposed to the electrolyte 20A.

The interlayer dielectric 68A may be any suitable insulator, including $SiO_2$, $HfO_2$, or $Al_2O_3$. When the interlayer dielectric 68A is silicon dioxide, etching may be performed to etch the various components of the nanopore sequencing device. For example, etching may be performed using an etchant with high anisotropy, such as fluorinated reactive ion etch including $CHF_3/O_2$, $C_2F_6$, $C_3F_8$, and $C_5F_8/CO/O_2/Ar$ as some non-limiting examples.

The membrane 24A may be any of the non-permeable or semi-permeable materials. The first nanoscale opening 23A extends through the membrane 24A. It is to be understood that the membrane 24A may be formed from any suitable natural or synthetic material, as described herein. In an example, the membrane 24A is selected from the group consisting of a lipid and a biomimetic equivalent of a lipid. In a further example, the membrane 24A is a synthetic membrane (e.g., a solid-state membrane, one example of which is silicon nitride), and the first nanoscale opening 23A is in a solid-state nanopore extending through the membrane 24A. In an example, the first nanoscale opening 23A extends through, for example: a polynucleotide nanopore; a polypeptide nanopore; or a solid-state nanopore, e.g., a carbon nanotube, disposed in the membrane.

In one example, the source, drain, and channel of the FET sensor 22A may be formed of silicon, and a surface of the silicon may be thermally oxidized to form a gate oxide on the channel of the FET sensor 22A.

The first nanopore 18A may be any of the biological nanopores, e.g., a protein nanopore, solid-state nanopores, hybrid nanopores, e.g., a hybrid protein/solid state nanopore, and synthetic nanopores. In some examples, the nanopore has two open ends and a hollow core or hole (i.e., the first nanoscale opening) that connects the two open ends. When inserted into the membrane, one of the open ends of the nanopore faces the cis well and the other of the open ends of the nanopore faces the middle well. In some instances, the open end of the nanopore that faces the middle well is fluidically connected to the fluidic tunnel and may also be aligned with at least a portion of the fluidic tunnel. In other instances, the open end of the nanopore that faces the middle well is fluidically connected to the fluidic tunnel, but is not aligned with the fluidic tunnel. The hollow core of the nanopore enables the fluidic and electrical connection between the cis well and the middle well. The diameter of the hollow core of the nanopore may range from about 1 nm up to about 1 µm, and may vary along the length of the nanopore. In some examples, the open end that faces the cis well may be larger than the open end that faces the middle well. In other examples, the open end that faces the cis well may be smaller than the open end that faces the middle well.

The first nanopore 18A may be inserted into the membrane directly, or the membrane may be formed around the nanopore. In an example, the nanopore may insert itself into a formed lipid bilayer membrane. For example, a nanopore in its monomeric form or polymeric form (e.g., an octamer) may insert itself into the lipid bilayer and assemble into a transmembrane pore. In another example, the nanopore may be added to a grounded side of a lipid bilayer at a desirable concentration where it will insert itself into the lipid bilayer. In still another example, the lipid bilayer may be formed across an aperture in a polytetrafluoroethylene (PTFE) film and positioned between the cis well and the middle well. The nanopore may be added to the grounded cis compartment, and may insert itself into the lipid bilayer at the area where the PTFE aperture is formed. In yet a further example, the nanopore may be tethered to a solid support (e.g., silicon, silicon oxide, quartz, indium tin oxide, gold, polymer, etc.). A tethering molecule, which may be part of the nanopore itself or may be attached to the nanopore, may attach the nanopore to the solid support. The attachment via the tethering molecule may be such that a single pore is immobilized (e.g., between the cis well and the middle well). A lipid bilayer may then be formed around the nanopore.

In an example, the second nanoscale opening inner diameter is at least about two times larger than the first nanoscale opening inner diameter. In another example, the second nanoscale opening inner diameter is about three times larger than the first nanoscale opening inner diameter. In yet another example, the second nanoscale opening inner diameter ranges from about two times larger than the first nanoscale opening inner diameter to about five times larger than the first nanoscale opening inner diameter. In an example, the area of the second nanoscale opening ranges from about five times to about 10 times larger than the area of the first nanoscale opening.

Further, in an example, the first nanoscale opening inner diameter ranges from about 0.5 nm to about 3 nm, and the second nanoscale opening inner diameter 25A ranges from about 10 nm to about 20 nm. In another example, the first nanoscale opening inner diameter 23A ranges from about 1 nm to about 2 nm, and the second nanoscale opening inner diameter 25A ranges from about 10 nm to about 20 nm. In yet another example, the first nanoscale opening inner diameter 23A ranges from about 1 nm to about 3 nm, and the second nanoscale opening inner diameter 25A ranges from about 2 nm to about 20 nm. The example ranges for the first nanoscale opening inner diameter 23A given above are intended to be the smallest diameter of the nanoscale opening 23A through the first nanopore 18A.

A substrate comprising an array of nanopore sequencing devices may have many different layouts of first nanoscale openings on the array, including regular, repeating, and non-regular patterns of nanoscale openings. In an example, the first nanoscale openings may be disposed in a hexagonal grid for close packing and improved density of the devices. Other array layouts may include, for example, rectilinear (i.e., rectangular) layouts, triangular layouts, and so forth. As examples, the layout or pattern can be an x-y format of first nanoscale openings that are in rows and columns. In some other examples, the layout or pattern can be a repeating arrangement of first nanoscale openings. In still other examples, the layout or pattern can be a random arrangement of first nanoscale openings. The pattern may include spots, posts, stripes, swirls, lines, triangles, rectangles, circles, arcs, checks, plaids, diagonals, arrows, squares, and/or cross-hatches.

The layout of nanoscale openings may be characterized with respect to the density of first nanoscale openings (i.e., number of first nanoscale openings in a defined area of the substrate comprising the array). For example, an array of first nanoscale openings may be present at a density ranging from about 10 first nanoscale openings per $mm^2$ to about 1,000,000 first nanoscale openings per $mm^2$. The density may also include, for example, a density of at least about 10 per $mm^2$, about 5,000 per $mm^2$, about 10,000 per $mm^2$, about 0.1 million per $mm^2$, or more. Alternatively or additionally, the density may no more than about 1,000,000 per $mm^2$, about 0.1 million per $mm^2$, about 10,000 per $mm^2$, about 5,000 per $mm^2$, or less. It is to be further understood that the density of the first nanoscale openings in the substrate can be between one of the lower values and one of the upper values selected from the ranges above.

The layout of first nanoscale openings in an array on a substrate may also be characterized in terms of the average pitch, i.e., the spacing from the center of a first nanoscale opening to the center of an adjacent first nanoscale opening (center-to-center spacing). The pattern can be regular such that the coefficient of variation around the average pitch is small, or the pattern can be non-regular in which case the coefficient of variation can be relatively large. In an example, the average pitch may range from about 100 nm to about 500 µm. The average pitch can be, for example, at least about 100 nm, about 5 µm, about 10 µm, about 100 µm, or more. Alternatively or additionally, the average pitch can be, for example, at most about 500 µm, about 100 µm, about 50 µm, about 10 µm, about 5 µm, or less. The average pitch for an example array of devices can be between one of the lower values and one of the upper values selected from the ranges above. In an example, the array may have a pitch (center-to-center spacing) of about 10 µm. In another example, the array may have a pitch (center-to-center spacing) of about 5 µm. In yet another example, the array may have a pitch (center-to-center spacing) ranging from about 1 µm to about 10 µm.

As mentioned above, a substrate for sequencing may include an array of nanopore sequencing devices. In one example of a nanopore sequencing device, the trans well is fluidically connected to the cis well by the middle well and the respective second and first nanoscale openings. In a substrate with an array of nanopore sequencing devices, there may be one common cis well and one common trans well communicating with a portion, or all, of the nanopore sequencing devices within the array on the substrate. However, it should be understood that an array of the nanopore devices may also include several cis wells that are fluidically isolated from one another and are fluidically connected to respective one or more trans wells fluidically isolated from one another and defined in the substrate. Multiple cis wells may be desirable, for example, in order to enable the measurement of multiple polynucleotides on a single substrate. In some embodiments, a substrate with an array of nanopore sequencing devices comprises one common cis electrode, one common trans electrode, one common cis well, one common trans well, and a plurality of nanopore sequencing devices, such as those shown in FIG. 2A where each nanopore sequencing device comprises a FET sensor and a dual pore with a first nanopore and a second nanopore. Each nanopore sequencing device of the plurality of nanopore sequencing devices can separately measure the resistance or signal by its associated FET sensor. In other embodiments, each nanopore sequencing device may comprise a multiple pore with three or more nanopores and a FET sensor. In other embodiments, the substrate with an array of nanopore sequencing devices comprises one common cis well, a plurality of trans wells, and a plurality of nanopore sequencing devices, where each nanopore sequencing device can be individually addressable with individual trans electrodes. In other embodiments, the substrate with an array of nanopore sequencing devices comprises a plurality of cis wells, a plurality of trans wells, and a plurality of nanopore sequencing devices, where each nanopore sequencing device can be individually addressable with individual trans electrodes.

The cis well of a nanopore sequencing device may be a fluid chamber that is defined, by sidewalls that are connected to the substrate. In some examples, the sidewalls and the substrate may be integrally formed, such that they are formed from a continuous piece of material (e.g., glass or plastic). In other examples, the sidewalls and the substrate may be separate components that are coupled to each other. In an example, the sidewalls are photo patternable polymers. In some examples, the cis well is formed within the space defined by the cis electrode, portions of the substrate, and the membrane. The cis well may have any suitable dimensions. In an example, the cis well ranges from about 1 mm×1 mm to about 3 cm×3 cm. The cis electrode, whose interior surface forms one surface of the cis well, may be physically connected to the sidewalls. The cis electrode may be physically connected to the sidewalls, for example, by an adhesive or another suitable fastening mechanism. The interface between the cis electrode and the sidewalls may seal the upper portion of the cis well.

The trans well of the nanopore sequencing device is a fluid chamber that may be defined in a portion of the substrate. The trans well may extend through the thickness of the substrate and may have openings at opposed ends of the substrate. In some examples, a trans well may have sidewalls that are defined by the substrate and/or by interstitial regions of the substrate, a lower surface that is defined by the trans electrode and an upper surface that is defined by a base structure. Thus, the trans well may be formed within the space defined by the trans electrode, the other portion and/or interstitial regions of the substrate, and the base structure. It is to be understood that the upper surface of the trans well may include the second nanoscale opening to provide fluid communication to the middle well. In some examples, the second nanoscale opening goes through the base structure. In some examples, the second nanoscale opening may be fluidically connected to and facing a narrower region of the trans well.

The trans well may be a micro well (having at least one dimension on the micron scale, e.g., about 1 µm up to, but not including, about 1000 µm) or nanowells (having the largest dimension on the nanoscale, e.g., about 10 nm up to, but not including, 1000 nm). The trans well may be characterized by its aspect ratio (e.g., width or diameter divided by depth or height in this example). In an example, the aspect ratio of the trans well may range from about 1:1 to about 1:5. In another example, the aspect ratio of each trans well may range from about 1:10 to about 1:50. In an example, the aspect ratio of the trans well is about 3.3. The depth/height and width/diameter of the trans well may be selected in order to obtain a desirable aspect ratio. The depth/height of each trans well can be at least about 0.1 µm, about 1 µm, about 10 µm, about 100 µm, or more. Alternatively or additionally, the depth can be at most about 1,000 µm, about 100 µm, about 10 µm, about 1 µm, about 0.1 µm, or less. The width/diameter of each trans well 16 can be at least about 50 nm, about 0.1 µm, about 0.5 µm, about 1 µm, about 10 µm, about 100 µm, or more. Alternatively or additionally, the width/diameter can be at most about 1,000 µm, about 100 µm, about 10 µm, about 1 µm, about 0.5 µm, about 0.1 µm, about 50 nm, or less.

The cis well and the trans well may be fabricated using a variety of techniques, including, for example, photolithography, nanoimprint lithography, stamping techniques, embossing techniques, molding techniques, microetching techniques, etc. As will be appreciated by those skilled in the art, the technique used will depend on the composition and shape of the substrate and the sidewalls. In an example, the cis well may be defined by one or more sidewalls at an end of the substrate, and the trans well may be defined through the substrate.

The trans electrode, whose interior surface is the lower surface of the trans well, may be physically connected to the substrate. The trans electrode may be fabricated in the process of forming the substrate (e.g., during the formation of the trans wells). Microfabrication techniques that may be used to form the substrate and the trans electrode include lithography, metal deposition and liftoff, dry and/or spin on film deposition, etching, etc. The interface between the trans electrode and the substrate may seal the lower portion of the trans well.

Examples of the material used to form the base structure 62A include silicon nitride ($Si_3N_4$), silicon carbide (SiC), aluminum oxide ($Al_2O_3$), hafnium oxide ($HfO_2$), and tantalum pentoxide ($Ta_2O_5$). Examples of suitable deposition techniques for these materials, in addition to CVD, include atomic layer deposition (ALD), or the like. Examples of suitable material combinations for the base structure 62A include $Si_3N_4$, $SiO_2$, SiC or $Al_2O_3$.

The cis electrode that is used depends, at least in part, upon the redox couple in the electrolyte. As examples, the cis electrode may be gold (Au), platinum (Pt), carbon (C) (e.g., graphite, diamond, etc.), palladium (Pd), silver (Ag), copper (Cu), or the like. In an example, the cis electrode may be a silver/silver chloride (Ag/AgCl) electrode. In one example, the cis well is capable of maintaining the electrolyte in contact with the first nanoscale opening. In some examples, the cis well may be in contact with an array of nanopores, and thus is capable of maintaining the electrolyte in contact with each of the nanopores in the array.

The trans electrode that is used depends, at least in part, upon the redox couple in the electrolyte. As examples, the trans electrode may be gold (Au), platinum (Pt), carbon (C) (e.g., graphite, diamond, etc.), palladium (Pd), silver (Ag), copper (Cu), or the like. In an example, the trans electrode may be a silver/silver chloride (Ag/AgCl) electrode.

In some examples, the relevant electrochemical half-reactions at the electrodes for a Ag/AgCl electrode in NaCl or KCl solution, are:

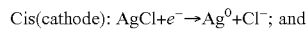

Cis(cathode): $AgCl + e^- \rightarrow Ag^0 + Cl^-$; and

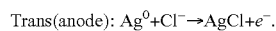

Trans(anode): $Ag^0 + Cl^- \rightarrow AgCl + e^-$.

For every unit charge of current, one Cl atom is consumed at the trans electrode. Though the discussion above is in terms of an Ag/AgCl electrode in NaCl or KCl solution, it is to be understood that any electrode/electrolyte pair that may be used to pass the current may apply.

In use, an electrolyte may be filled into the cis well, the middle well, the fluidic tunnel, the narrower region, and the trans well. In alternative examples, the electrolyte in the cis well, the middle well, and the trans well may be different. The electrolyte may be any electrolyte that is capable of dissociating into counter ions (a cation and its associated anion). As examples, the electrolyte may be an electrolyte that is capable of dissociating into a potassium cation ($K^+$) or a sodium cation ($Na^+$). This type of electrolyte includes a potassium cation and an associated anion, or a sodium cation and an associated anion, or combinations thereof. Examples of potassium-containing electrolytes include potassium chloride (KCl), potassium ferricyanide ($K_3[Fe(CN)_6] \cdot 3H_2O$ or $K_4[Fe(CN)_6] \cdot 3H_2O$), or other potassium-containing electrolytes (e.g., bicarbonate ($KHCO_3$) or phosphates (e.g., $KH_2PO_4$, $K_2HPO_4$, $K_3PO_4$). Examples of sodium-containing electrolytes include sodium chloride (NaCl) or other sodium-containing electrolytes, such as sodium bicarbonate ($NaHCO_3$), sodium phosphates (e.g., $NaH_2PO_4$, $Na_2HPO_4$ or $Na_3PO_4$). As another example, the electrolyte may be any electrolyte that is capable of dissociating into a ruthenium-containing cation (e.g., ruthenium hexamine, such as $[Ru(NH_3)_6]^{2+}$ or $[Ru(NH_3)_6]^{3+}$). Electrolytes that are capable of dissociating into a lithium cation ($Li^+$), a rubidium cation ($Rb^+$), a magnesium cation ($Mg^+$), or a calcium cation (Ca) may also be used.

In examples wherein a plurality of nanopore sequencing devices forms an array on a substrate, each of the plurality of the nanopore sequencing devices in the array may share a common cis electrode and a common trans electrode. In another example, each of the plurality of the nanopore sequencing devices shares a common cis electrode, but has a distinct trans electrode. In yet another example, each of the plurality of the nanopore sequencing devices has a distinct cis electrode and a distinct trans electrode. In still another example, each of the plurality of nanopore sequencing devices has a distinct cis electrode and shares a common trans electrode. As the array of nanopore devices is scaled, the volume of each trans well typically depletes as the $3^{rd}$ power of the well dimension (assuming that a constant aspect ratio is maintained). In some example, an array lifetime is about or above 48 hours, and a typical diameter of the trans well is about or above 100 µm.

Alternate Examples

Figure 3A:
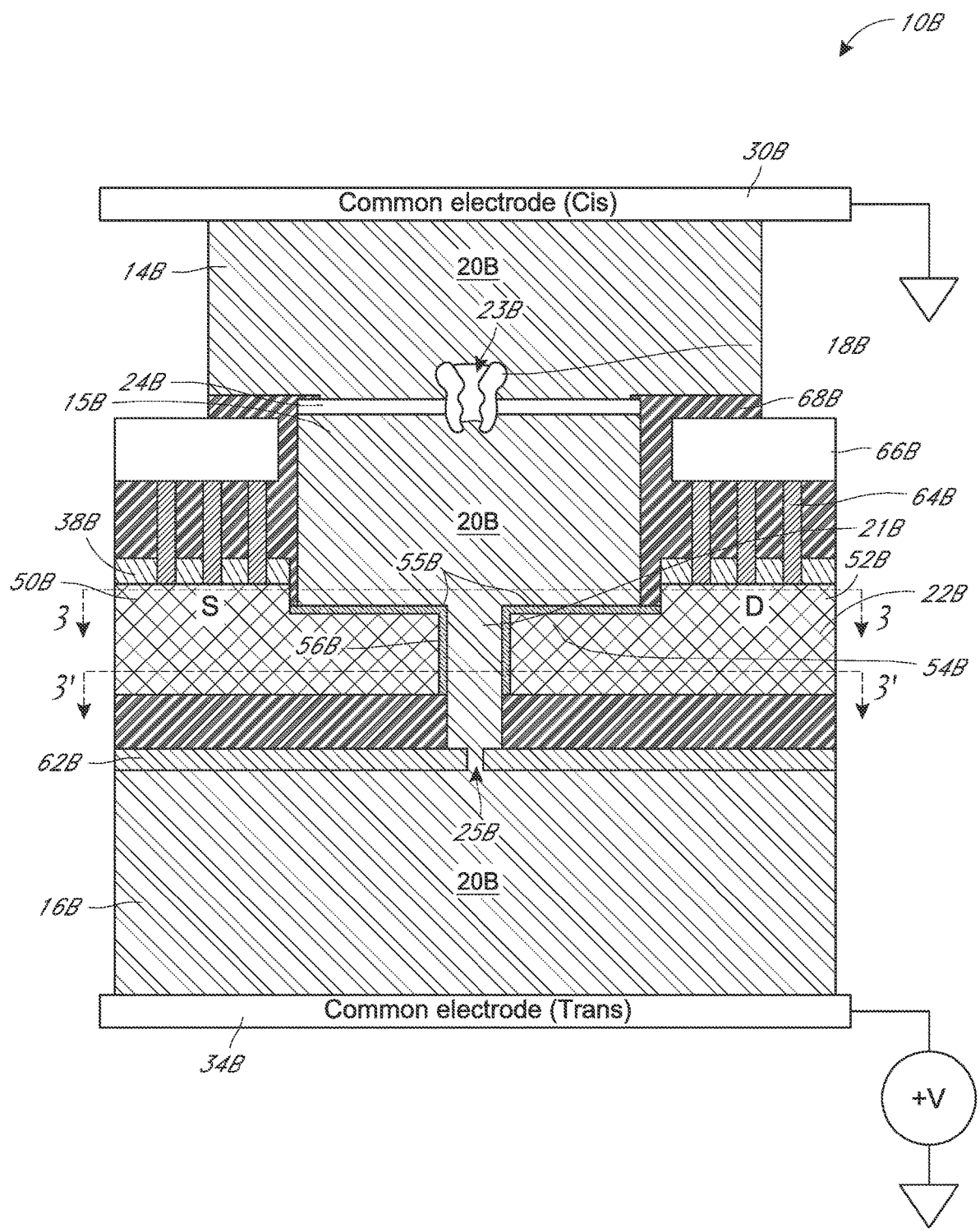
FIG. 3A shows a cross-sectional side view of an alternate example of a nanopore sequencing device according to one example.

FIG. 3A shows a variation of the device 10A illustrated in FIG. 2A. As shown in FIG. 3A, a nanopore sequencing device 10B includes similar components with the device shown in FIG. 2A. However, the substrate material 62B shown in FIG. 3A does not have a narrower region as was illustrated in FIG. 2A. The substrate material 62B is more planar in format.

Figure 3B:
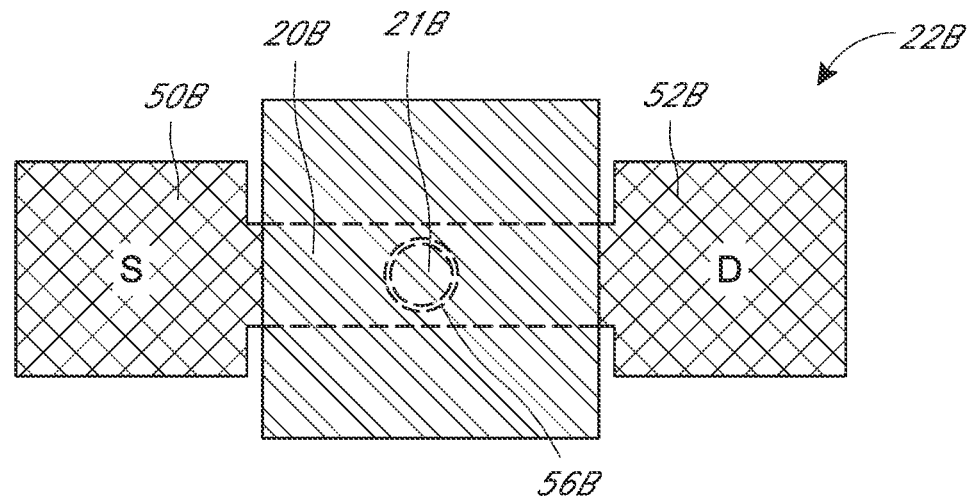
FIG. 3B is a cross-sectional top view, taken on line 3-3 of the nanopore sequencing device of FIG. 3A and a FET sensor.
Figure 3C:
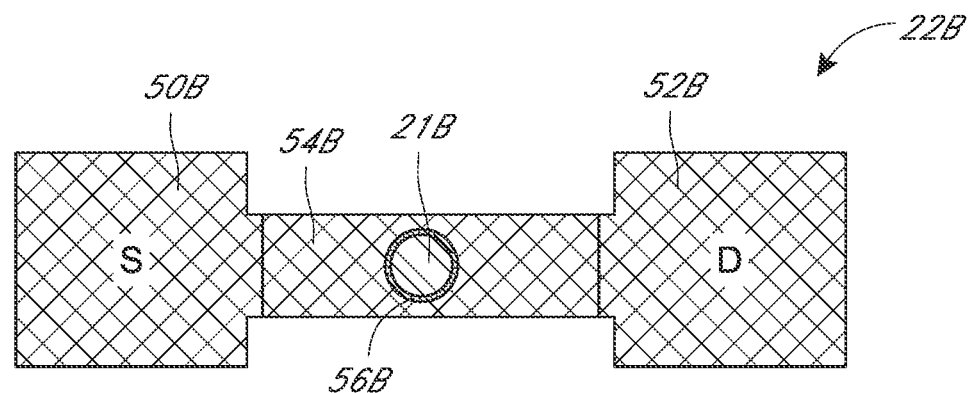
FIG. 3C is a cross-sectional top view, taken on line 3'-3' of the nanopore sequencing device of FIG. 3A and a FET sensor.

The nanopore sequencing device 10B is shown in FIGS. 3A, 3B, and 3C includes a cis electrode 30B connecting to a cis well 14B. The cis well 14B has a lower portion that includes a first nanopore 18B disposed into a membrane 24B. The first nanopore 18B includes a first nanoscale opening 23B defined by the first nanopore 18B that communicates with a fluidic tunnel 21B to a second nanoscale opening 25B between the fluidic tunnel 21B and a trans well 16B at a lower portion of the device 10B. As shown, the second nanoscale opening 25B is formed in the substrate material 62B. The first nanopore 18B provides a fluidic pathway for electrolyte 20B to pass between the cis well 14B and the middle well 15B. The fluidic tunnel 21B provides a fluidic pathway for the electrolyte to pass from the middle well 15B, through the second nanoscale opening 25B and to the trans well 16B. In use, an electrolyte may be filled into the cis well 14B, the middle well 15B, and the trans well 16B. In alternative examples, the electrolyte in the cis well 14B, the middle well 15B, and the trans well 16B may be different. In some examples, the diameter of the first nanoscale opening 23B may be equal to or smaller than the opening of the fluidic tunnel 21B. A substrate for sequencing may include an array of nanopore sequencing devices. In one example of a nanopore sequencing device, the trans well is fluidically connected to the cis well by the middle well and the respective second and first nanoscale openings. In a substrate with an array of nanopore sequencing devices, there may be one common cis well and one common trans well communicating with a portion, or all, of the nanopore sequencing devices within the array on the substrate. However, it should be understood that an array of the nanopore devices may also include several cis wells that are fluidically isolated from one another and are fluidically connected to respective one or more trans wells fluidically isolated from one another and defined in the substrate. Multiple cis wells may be desirable, for example, in order to enable the measurement of multiple polynucleotides on a single substrate. In some embodiments, a substrate with an array of nanopore sequencing devices comprises one common cis electrode, one common trans electrode, one common cis well, one common trans well, and a plurality of nanopore sequencing devices, such as those shown in FIG. 3A where each nanopore sequencing device comprises a FET sensor and a dual pore with a first nanopore and a second nanopore. Each nanopore sequencing device of the plurality of nanopore sequencing devices can separately measure the resistance or signal by its associated FET sensor. In other embodiments, each nanopore sequencing device may comprise a multiple pore with three or more nanopores and a FET sensor. In other embodiments, the substrate with an array of nanopore sequencing devices comprises one common cis well, a plurality of trans wells, and a plurality of nanopore sequencing devices, where each nanopore sequencing device can be individually addressable with individual trans electrodes. In other embodiments, the substrate with an array of nanopore sequencing devices comprises a plurality of cis wells, a plurality of trans wells, and a plurality of nanopore sequencing devices, where each nanopore sequencing device can be individually addressable with individual trans electrodes.

In one example, the cis electrode 30B and the trans electrode 34B are at least substantially parallel to one another in an at least substantially horizontal direction. In other examples, the cis electrode and the trans electrode may be in any suitable orientation relative to each other and to the nanopore device. The nanopore device 10B further includes a field effect transistor (FET) sensor 22B positioned between the first nanoscale opening 23B and the second nanoscale opening 25B. The FET sensor includes a source (S) 50B, a drain (D) 52B, and a channel 54B that connects the source 50B to the drain 52B. As shown in top views, FIGS. 3B and 3C, the electrolyte 20B can be seen in the fluidic tunnel 21B and extending through the channel 54B. Metallic interconnects 64B and 66B are in electrical communication with the source 50B and drain 52B of the FET 22B, through the etch stop layer 38B. The metallic interconnects 64B and 66B communicate data from the FET sensor 22B to a control system monitoring the FET sensor 22B.

In the example of the nanopore device 10B shown in FIG. 3A, a thin layer of gate oxide 56B is grown around the channel 54B; therefore, its upper surface 55B is fluidically exposed to the middle well 15B. The gate oxide 56B may have a vertical surface fluidically exposed to the electrolyte 20B in the fluidic tunnel 21B. The thin layer of gate oxide separates the channel 54B from the electrolyte 20B and exposes the channel 54B of the FET sensor 22B to the electrolyte 20B. In addition to exposing the channel 54B to the variation in voltage through the gate oxide 56B at the boundary of the fluidic tunnel 21B, the structure with the exposed upper surface 55B as shown in FIGS. 3A, 3B and 3C greatly increases the sensing area of the FET exposed to $\delta V_M$ and improves the LoD. The thickness of the gate oxide 56B may be between about 1 and about 10 nm in thickness, and in some examples between about 2 and about 4 nm in thickness. The thickness of the gate oxide 56B is chosen such that a strong enough electric field, given the potential $V_M$, can induce an inversion layer of electrons or holes which constitutes a conductive path at the channel 54B-gate oxide 56B boundary to conduct between the source 50B and drain 52B.

The interlayer dielectric 68B may be any suitable insulator, including $SiO_2$, $HfO_2$, or $Al_2O_3$. When the interlayer dielectric 68B is silicon dioxide, etching may be performed to etch the various components of the nanopore sequencing device. For example, etching may be performed using an etchant with high anisotropy, such as fluorinated reactive ion etch including $CHF_3/O_2$, $C_2F_6$, $C_3F_8$, and $C_5F_8/CO/O_2/Ar$ as some non-limiting examples.

As illustrated, the trans well 16 in FIG. 3A does not include a narrower region as compared to FIG. 2A. In some instances, this allows for a larger trans well 16B. The basic operating principle remains the same for the remainder of the nanopore sequencing device.

FIG. 3B and FIG. 3C are cross-sectional top views, taken in FIG. 3A on line 3-3 and line 3'-3', respectively, showing an example of the FET sensor which is a nanowire transistor, i.e., the channel 54B has a nanowire configuration.

In the nanowire transistor, the channel 54B has a length along a direction from the source 50B to the drain 52B, a height along a direction from the cis electrode 30B to the trans electrode 34B, and a width along a direction at least partially or substantially orthogonal to both the length and the height. In one example, the length may be at least about 10 times the width or the height. The intersection between the fluidic tunnel 21B and the channel 54B, in a plane defined by the length and the width, may be disc shaped as shown in FIG. 3B and FIG. 3C.

The LoD of a nanowire transistor having an about 250 nm×20 nm×30 nm nanowire is about 3 mV, while the LoD of a nanowire transistor having an about 10,000 nm×100 nm×30 nm wire is about 0.2 mV.

Figure 3D:
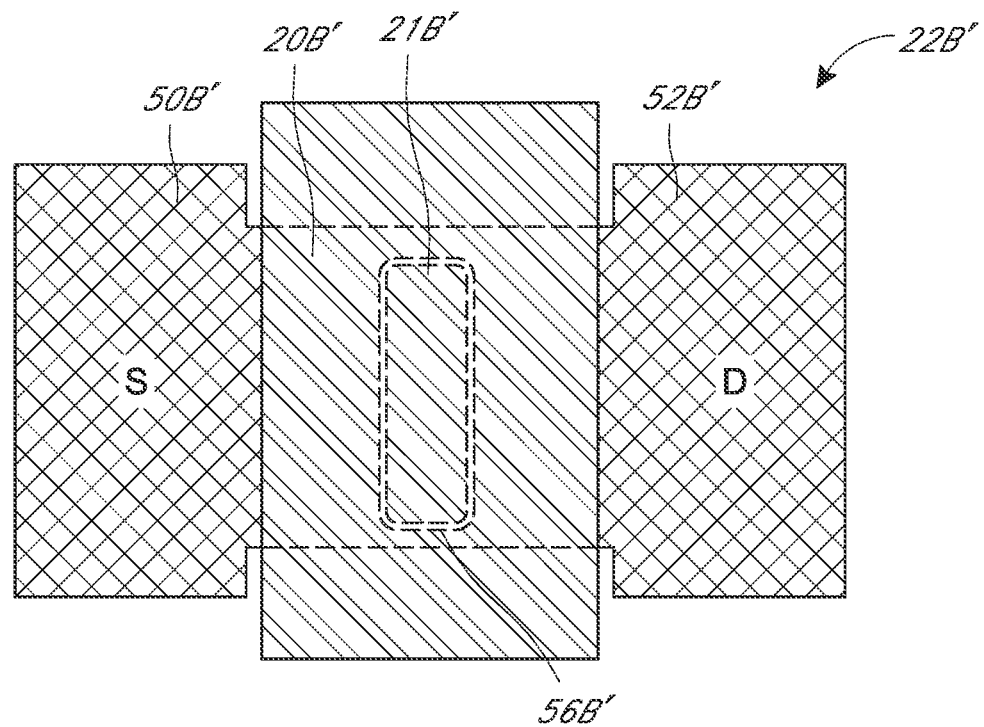
FIG. 3D is an alternate example of a cross-sectional top view, taken on line 3-3 of a nanopore sequencing device similar to FIG. 3A, but with a wider example of a FET sensor.
Figure 3E:
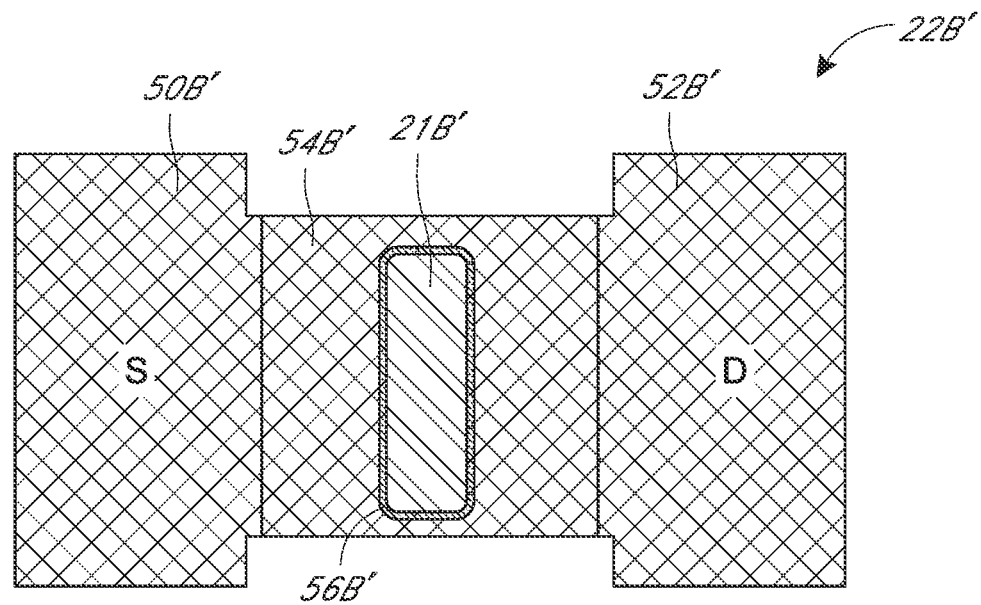
FIG. 3E is an alternate example of a cross-sectional top view, taken on line 3'-3' of a nanopore sequencing device similar to FIG. 3A, but with a wider example of a FET sensor.

FIG. 3D and FIG. 3E are cross-sectional top views of a nanosheet FET sensor 22B', as compared to the nanowire FET sensor 22B shown in FIGS. 3B and 3C. In the nanosheet FET sensor 22B', the channel 54B' has a nanosheet configuration. A thin layer of gate oxide 56B' separates the upper surface of the channel 54B' from the electrolyte 20B' and exposes the channel 54B' of the FET sensor 22B' to the electrolyte 20B'. The thickness of the gate oxide 56B' may be about 1-about 10 nm, preferably about 2-about 4 nm. The thickness of the gate oxide 56B' is chosen such that a strong enough electric field, given the potential $V_M$, can induce an inversion layer of electrons or holes which constitutes a conductive path at the channel 54B'-gate oxide 56B' boundary to conduct between the source 50B' and drain 52B'. The sensing area of the FET exposed to the electrolyte 20B' is greatly increased, thus further improving the LoD.

In the nanosheet FET sensor 22B', the channel 54B' has a length along a direction from a source 50B' to a drain 52B', a height along a direction from the cis electrode to the trans electrode, and a width along a direction at least partially or substantially orthogonal to both the length and the height. The length may be at least about 2 times the height, and the width may be at least about 2 times the height. In other examples length may be at least about 3, about 4, about 5, about 6, about 7, about 8, about 9, about 10 or more times the height, and the width may be at least about 3, about 4, about 5, about 6, about 7, about 8, about 9, about 10 or more times the height. The intersection between the fluidic tunnel 21B' and the channel 54B', in a plane defined by the length and the width, may be oblong shaped as shown in FIG. 3D and FIG. 3E (for example, see the oblong shaped boundary of 56B').

Alternatively, the intersection between the fluidic tunnel 21B' and the channel 54B' in a nanosheet transistor can be of nearly arbitrary shape and size, potentially increasing the sensing area of the FET even further and thus driving the LoD down even further. Since the size and shape requirement of the fluidic tunnel may be relaxed, the manufacturability of the device may be improved.

Additional Examples

FIGS. 4A, 4B, and 4B' illustrate another example of the nanopore device shown in FIGS. 2A, 2B, and 2B', which uses a gate-all-around (GAA) transistor. FIG. 4A is a cross-sectional side view of a nanopore sequencing device 10C. FIG. 4B is a cross-sectional top view, taken on line 3-3 in FIG. 4A. FIG. 4B' is a cross-sectional top view, taken on line 3'-3' in FIG. 4A.

The nanopore sequencing device 10C shown in FIGS. 4A, 4B, and 4B' includes a cis electrode 30C connecting to a cis well 14C. The cis well 14C has a lower portion that includes a first nanopore 18C disposed into a membrane 24C. The first nanopore 18C includes a first nanoscale opening 23C defined by the first nanopore 18C that communicates with a fluidic tunnel 21C to a second nanoscale opening 25C disposed in a narrower region 17C between the fluidic tunnel 21C and a trans well 16C at a lower portion of the device 10C. As shown, the second nanoscale opening is formed in the substrate material 62C. The first nanopore 18C provides a fluidic pathway for electrolyte 20C to pass between the cis well 14C and the middle well 15C. The fluidic tunnel 21C provides a fluidic pathway for the electrolyte to pass from the middle well 15C, through the second nanoscale opening 25C and to the trans well 16C. A substrate for sequencing may include an array of nanopore sequencing devices. In one example of a nanopore sequencing device, the trans well is fluidically connected to the cis well by the middle well and the respective second and first nanoscale openings. In a substrate with an array of nanopore sequencing devices, there may be one common cis well and one common trans well communicating with a portion, or all, of the nanopore sequencing devices within the array on the substrate. However, it should be understood that an array of the nanopore devices may also include several cis wells that are fluidically isolated from one another and are fluidically connected to respective one or more trans wells fluidically isolated from one another and defined in the substrate. Multiple cis wells may be desirable, for example, in order to enable the measurement of multiple polynucleotides on a single substrate. In some embodiments, a substrate with an array of nanopore sequencing devices comprises one common cis electrode, one common trans electrode, one common cis well, one common trans well, and a plurality of nanopore sequencing devices, such as those shown in FIG. 4A where each nanopore sequencing device comprises a FET sensor and a dual pore with a first nanopore and a second nanopore. Each nanopore sequencing device of the plurality of nanopore sequencing devices can separately measure the resistance or signal by its associated FET sensor. In other embodiments, each nanopore sequencing device may comprise a multiple pore with three or more nanopores and a FET sensor. In other embodiments, the substrate with an array of nanopore sequencing devices comprises one common cis well, a plurality of trans wells, and a plurality of nanopore sequencing devices, where each nanopore sequencing device can be individually addressable with individual trans electrodes. In other embodiments, the substrate with an array of nanopore sequencing devices comprises a plurality of cis wells, a plurality of trans wells, and a plurality of nanopore sequencing devices, where each nanopore sequencing device can be individually addressable with individual trans electrodes.

In one example, the cis electrode 30C and the trans electrode 34C are at least substantially parallel to one another in an at least substantially horizontal direction. In other examples, the cis electrode and the trans electrode may be in any suitable orientation relative to each other and to the nanopore device. The nanopore device 10C further includes a field effect transistor (FET) sensor 22C positioned between the first nanoscale opening 23C and the second nanoscale opening 25C. The FET sensor includes a source (S) 50C, a drain (D) 52C, and a channel 54C that connects the source 50C to the drain 52C. As shown in top views, FIGS. 4B and 4B', the electrolyte 20C can be seen in the fluidic tunnel 21C and extending through the channel 54C. Metallic interconnects 66C and 64C are in electrical communication with the source 50C and drain 52C of the FET 22C, through the etch stop layer 38C. The metallic interconnects communicate data from the FET sensor 22C to a control system monitoring the FET sensor 22C.

In the nanopore sequencing device 10C shown in FIG. 4A, the bulk of the material right above line 3-3 separating the channel 54C from the electrolyte 20C is removed, exposing the channel 54C of the FET sensor 22C to the electrolyte 20C. In addition, the bulk of the material right below the channel 54C is removed, or hollowed out, exposing the channel 54C to the electrolyte from below as well—this may be formed by undercutting the active area 54C of the FET sensor 22C by well-known methods. Only a thin layer of gate oxide 56C is grown around the channel 54C. An upper surface 55C and a lower surface 58C of the gate oxide 56C are fluidically exposed to the electrolyte 20C in the middle well 15C and fluidic channel 21C. The gate oxide 56C may have a vertical surface fluidically exposed to the electrolyte 20C in the fluidic tunnel 21C. The thin layer of gate oxide 56C separates the channel 54C from the electrolyte 20C and exposes the channel 54C of the FET sensor 22C to the electrolyte 20C. The thickness of the gate oxide 56C may be between about 1 and about 10 nm, and in some examples between about 2 and about 4 nm. The thickness of the gate oxide 56C is chosen such that a strong enough electric field, given the potential $V_M$, can induce an inversion layer of electrons or holes which constitutes a conductive path at the channel 54C-gate oxide 56C boundary to conduct between the source 50C and drain 52C.

Such a configuration of the FET sensor 22C shown in FIG. 4A allows the exposure of a relatively large area of the channel 54C to the electrolyte 20C (as compared to FIG. 2A). The channel 54C therefore uses the upper surface 55C and lower surface 58C for fluidically connecting the channel 54C to the middle well 15C. Therefore, the potential $V_M$ has advantageous gate controllability over the channel 54C, and further reduces the LoD. In addition to exposing the channel 54C to the variation in voltage through the gate oxide 56C at the boundary of the fluidic tunnel 21C, the structure of the FET sensor 22C with the exposed upper surface 55C and lower surface 58C as shown in FIGS. 4A, 4B and 4B' greatly increases the sensing area of the FET exposed to $\delta V_M$ and improves the LoD.

The interlayer dielectric 68C may be any suitable insulator, such as $SiO_2$, $HfO_2$ or $Al_2O_3$. When the interlayer dielectric 68C is silicon dioxide, etching may be performed to etch the various components of the nanopore sequencing device. For example, etching may be performed using an etchant with high anisotropy, such as fluorinated reactive ion etch including $CHF_3/O_2$, $C_2F_6$, $C_3F_8$, and $C_5F_8/CO/O_2/Ar$ as some non-limiting examples.

The membrane 24C may be any of the non-permeable or semi-permeable materials. The first nanoscale opening 23C extends through the membrane 24C. It is to be understood that the membrane 24C may be formed from any suitable natural or synthetic material, as described herein. In an example, the membrane 24C is selected from the group consisting of a lipid and a biomimetic equivalent of a lipid. In a further example, the membrane 24C is a synthetic membrane (e.g., a solid-state membrane, one example of which is silicon nitride), and the first nanoscale opening 23C is in a solid-state nanopore extending through the membrane 24C. In an example, the first nanoscale opening 23C extends through, for example: a polynucleotide nanopore; a polypeptide nanopore; or a solid-state nanopore, e.g., a carbon nanotube, disposed in the membrane.

In one example, the source, drain, and channel of the FET sensor 22C may be formed of silicon, and a surface of the silicon may be thermally oxidized to form a gate oxide on the channel of the FET sensor 22C.

The first nanopore 18C may be any of the biological nanopores, solid-state nanopores, hybrid nanopores, and synthetic nanopores. In some examples, the first nanopore 18C has two open ends and a hollow core or hole (i.e., the first nanoscale opening 23C) that connects the two open ends. When inserted into the membrane 24C, one of the open ends of the first nanopore 18C faces the cis well 14C and the other of the open ends of the first nanopore 18C faces the middle well 15C. In some instances, the open end of the first nanopore 18C that faces the middle well 15C is fluidically connected to the fluidic tunnel 21C and may also be aligned with at least a portion of the fluidic tunnel 21C. In other instances, the open end of the first nanopore 18C that faces the middle well 15C is fluidically connected to the fluidic tunnel 21C, but is not aligned with the fluidic tunnel 21C. The hollow core of the first nanopore 18C enables the fluidic and electrical connection between the cis well 14C and the middle well 15C. The diameter of the hollow core of the first nanopore 18C may range from about 1 nm up to about 1 μm, and may vary along the length of the first nanopore 18C. In some examples, the open end that faces the cis well 14C may be larger than the open end that faces the middle well 15C. In other examples, the open end that faces the cis well 14C may be smaller than the open end that faces the middle well 15C.

Further Examples

Figure 5A:
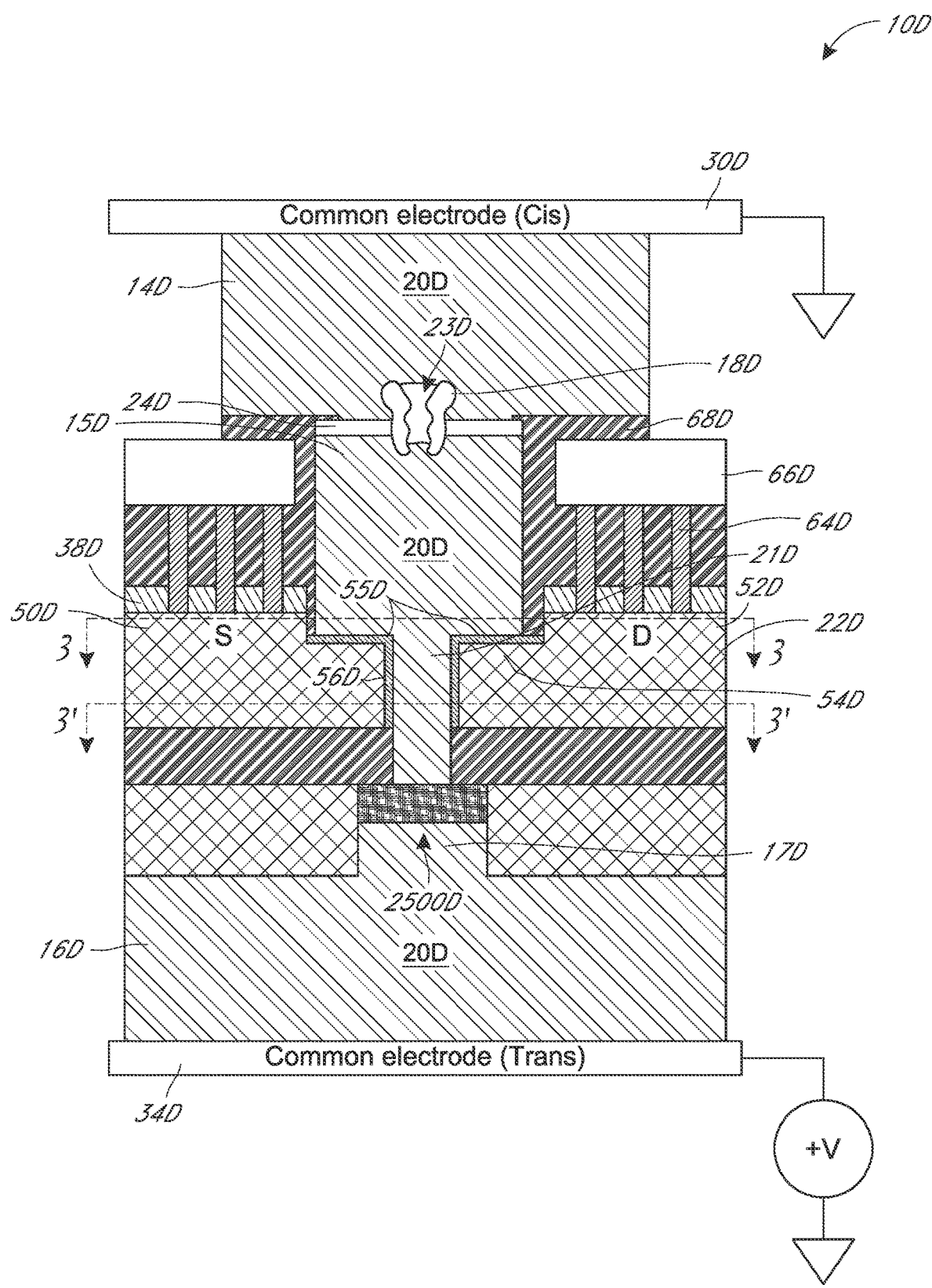
FIG. 5A is cross-sectional side view of yet another alternate example of a nanopore sequencing device.
Figure 5B:
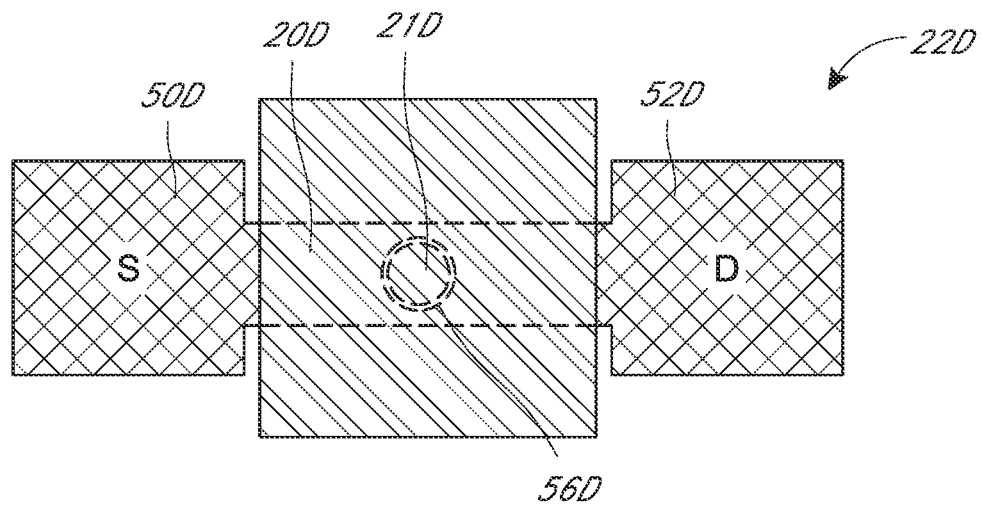
FIG. 5B is a cross-sectional top view, taken on line 3-3 of the nanopore sequencing device of FIG. 5A.
Figure 5B:
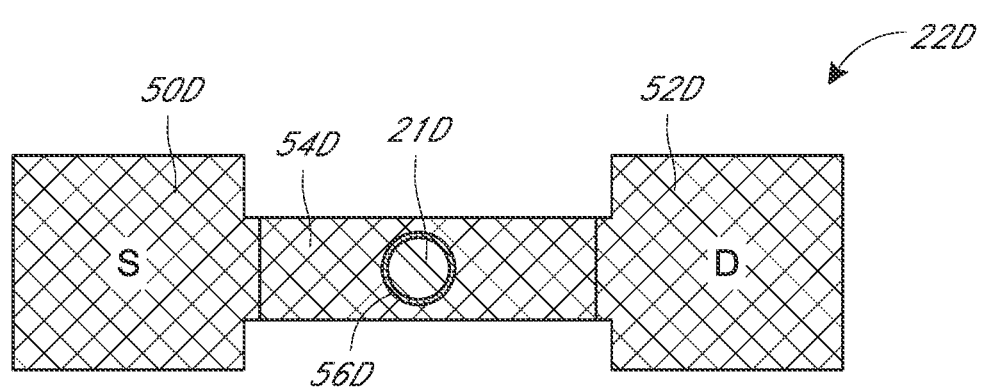

FIGS. 5A, 5B, and 5B' illustrate a modification to the nanopore device shown in FIGS. 2A, 2B, and 2B', which uses a porous structure 2500D in lieu of a second nanoscale opening 25A shown in FIG. 2A. FIG. 5A is a side cross-sectional view of the modified exemplary device 10D. FIG. 5B is a cross-sectional top view, taken on line 3-3 in FIG. 5A. FIG. 5B' is a cross-sectional top view, taken on line 3'-3' in FIG. 5A.

The nanopore sequencing device 10D shown in FIGS. 5A, 5B, and 5B' includes a cis electrode 30D connecting to a cis well 14D. The cis well 14D has a lower portion that includes a first nanopore 18D disposed into a membrane 24D. The first nanopore 18D includes a first nanoscale opening 23D defined by the first nanopore 18D that communicates with a fluidic tunnel 21D to a narrower region 17D of a trans well 18D at a lower portion of the device 10D. The first nanopore 18D provides a fluidic pathway for electrolyte 20D to pass between the cis well 14D and the middle well 15D. The fluidic tunnel 21D provides a fluidic pathway for the electrolyte to pass from the middle well 15D to the trans well 18D. A porous structure 2500D is disposed between the trans well 18D and the middle well 15D. A substrate for sequencing may include an array of nanopore sequencing devices. In one example of a nanopore sequencing device, the trans well is fluidically connected to the cis well by the middle well and the respective second and first nanoscale openings. In a substrate with an array of nanopore sequencing devices, there may be one common cis well and one common trans well communicating with a portion, or all, of the nanopore sequencing devices within the array on the substrate. However, it should be understood that an array of the nanopore devices may also include several cis wells that are fluidically isolated from one another and are fluidically connected to respective one or more trans wells fluidically isolated from one another and defined in the substrate. Multiple cis wells may be desirable, for example, in order to enable the measurement of multiple polynucleotides on a single substrate. In some embodiments, a substrate with an array of nanopore sequencing devices comprises one common cis electrode, one common trans electrode, one common cis well, one common trans well, and a plurality of nanopore sequencing devices, such as those shown in FIG. 5A where each nanopore sequencing device comprises a FET sensor and a dual pore with a first nanopore and a second nanopore. Each nanopore sequencing device of the plurality of nanopore sequencing devices can separately measure the resistance or signal by its associated FET sensor. In other embodiments, each nanopore sequencing device may comprise a multiple pore with three or more nanopores and a FET sensor. In other embodiments, the substrate with an array of nanopore sequencing devices comprises one common cis well, a plurality of trans wells, and a plurality of nanopore sequencing devices, where each nanopore sequencing device can be individually addressable with individual trans electrodes. In other embodiments, the substrate with an array of nanopore sequencing devices comprises a plurality of cis wells, a plurality of trans wells, and a plurality of nanopore sequencing devices, where each nanopore sequencing device can be individually addressable with individual trans electrodes.

In one example, the cis electrode 30D and the trans electrode 34D are at least substantially parallel to one another in an at least substantially horizontal direction. In other examples, the cis electrode and the trans electrode may be in any suitable orientation relative to each other and to the nanopore device. The nanopore device 10D further includes a field effect transistor (FET) sensor 22D positioned between the first nanoscale opening 23D and the porous structure 2500D. The FET sensor includes a source (S) 50D, a drain (D) 52D, and a channel 54D that connects the source 50D to the drain 52D. As shown in top views, FIGS. 5B and 5B', the electrolyte 20D can be seen in the fluidic tunnel 21D and extending through the channel 54D. Metallic interconnects 66D and 64D are in electrical communication with the source 50D and drain 52D of the FET 22D, through the etch stop layer 38D. The metallic interconnects 66D and 64D communicate data from the FET sensor 22D to a control system monitoring the FET sensor 22D.

In the example of the nanopore device 10D shown in FIG. 5A, a thin layer of gate oxide 56D is grown around the channel 54D; therefore, its upper surface 55D is fluidically exposed to the middle well. The gate oxide 56D may have a vertical surface fluidically exposed to the electrolyte 20D in the fluidic tunnel 21D. The gate oxide separates the channel 54D from the electrolyte 20D and exposes the channel 54D of the FET sensor 22D to the electrolyte 20D. The thickness of the gate oxide 56D may be between about 1 and about 10 nm, and in some examples between about 2 and about 4 nm. The thickness of the gate oxide 56D is chosen such that a strong enough electric field, given the potential $V_M$, can induce an inversion layer of electrons or holes which constitutes a conductive path at the channel 54D-gate oxide 56D boundary to conduct between the source 50D and drain 52D.

In this configuration, the channel 54D has an upper surface fluidically connecting the channel 54D to the electrolyte in the middle well 15D, as shown in FIG. 5B. By increasing the area of the channel 54D exposed to the electrolyte 20D, the potential $V_M$ has a better gate controllability over the channel 54D. In addition to exposing the channel 54D to the variation in voltage through the gate oxide 56D at the boundary of the fluidic tunnel 21D, the structure with the exposed upper surface of the channel 54D as shown in FIGS. 5A, 5B and 5B' greatly increases the sensing area of the FET exposed to $\delta V_M$ and improves the LoD.

In FIG. 2A, the second nanoscale opening 25A, e.g., formed in a solid-state nanopore, defines part of the operation of the device. Using current complementary metal-oxide-semiconductor (CMOS)-technologies to make nanopores of less than about 10 nm may be a challenge. However, this choice limits the divider ratio D to ~0.1, which in turn reduces the variation δD when the base of the polynucleotide at the first nanoscale opening 23 changes, which in turn drives up the required cis-trans bias V. In certain embodiments, the equivalent circuit of the nanopore device satisfies the following equations.

In the device 10A of FIG. 2A, the signal detected by the FET sensor is proportional to $$\frac{\partial D}{\partial R_{protein}} = \frac{1}{R_{protein} + R_{pore}} - \frac{R_{protein}}{(R_{protein} + R_{pore})^2}. \quad (6)$$

This signal is maximized when $$\frac{\partial^2 D}{\partial R_{pore} \partial R_{protein}} = 0, \quad (7)$$

which translates to a requirement that $$R_{pore} = R_{protein}. \quad (8)$$

Fabricating a solid-state nanopore with size and resistance similar to that of a protein nanopore remains challenging for current CMOS-based fabrication technology. Furthermore, a single solid-state nanopore meeting this requirement may have a resistance that varies, since the polynucleotide, e.g., a single-stranded DNA polymer, with a width of about 1 nm, is expected to significantly alter the resistance if it traverses the solid-state nanopore that has an opening of similar width.

In contrast, in FIG. 5A, the second nanoscale opening is replaced with a porous structure 2500D, e.g., a nanoporous frit or membrane. The structure and function of the frit is similar to that of glass frits used in reference electrodes. The pores in the frit may be randomly distributed and may form complicated pathways. The porosity of the frit is selected so that it is sufficient to establish electrical continuity across the frit (i.e., big enough to allow ionic species from the electrolyte to pass), but small enough so that significant resistance to ionic current is established. The resistance of typical frits having a 1 mm² in size is on the order of 1 MΩ. Therefore, a 100 nm×100 nm frit may be expected to have a resistance of >1 TΩ. Typical frits have pore sizes of about a few nm and thickness of about 1 mm. Tuning the porosity and thickness of the frit should allow achieving the desired target of $$R_{frit} = R_{protein} \quad (9)$$

There are numerous fabrication compatible materials that may be used for the frit. low-κ dielectrics, such as porous low-κ dielectrics (e.g., organosilicate glass (SiCOH), such as porous organosilicate glass (SiCOH)), may be used and fabricated to have porosities that can be tuned as high as 50%. Precursors with ring structures such as cyclomethicone, e.g., decamethylcyclopentasiloxane ($[(CH_3)_2SiO]_5$), are sometimes used to achieve an intrinsic porosity of a few percent. Porosities as high as 50% can be achieved from dual-phase precursors such as mixtures of DMDS (dimethyl disulfide, $CH_3SSCH$) and α-terpenine, where the α-terpenine phase is removed via thermal treatment. The structure of the resulting material can vary from worm-like mesopores arranged in a disorderly fashion to well-ordered channel-like arrays, with typical pore size of about a few nm. Ordered porosity with periods of about tens of nm has also been demonstrated.

Additional Example

FIG. 6 is a cutaway, schematic and partially cross-sectional view of yet another exemplary nanopore sequencing device 10E. FIG. 6 illustrates a modification of FIG. 5A, where the FET sensor further improves the SNR and gate controllability by using a stack of channels 601.

The nanopore sequencing device 10E shown in FIG. 6 includes a cis electrode 30E connecting to a cis well 14E. The cis well 14E has a lower portion that includes a first nanopore 18E disposed into a membrane 24E. The first nanopore 18E includes a first nanoscale opening 23E defined by the first nanopore 18E that communicates with a fluidic tunnel 21E to a narrower region 17E of a trans well 16E at a lower portion of the device 10E. The first nanopore 18E provides a fluidic pathway for electrolyte 20E to pass between the cis well 14E and the middle well 15E. The fluidic tunnel 21E provides a fluidic pathway for the electrolyte to pass from the middle well 15E to the trans well 16E. A porous structure 2500E is disposed between the trans well 16E and the middle well 15E. A substrate for sequencing may include an array of nanopore sequencing devices. In one example of a nanopore sequencing device, the trans well is fluidically connected to the cis well by the middle well and the respective second and first nanoscale openings. In a substrate with an array of nanopore sequencing devices, there may be one common cis well and one common trans well communicating with a portion, or all, of the nanopore sequencing devices within the array on the substrate. However, it should be understood that an array of the nanopore devices may also include several cis wells that are fluidically isolated from one another and are fluidically connected to respective one or more trans wells fluidically isolated from one another and defined in the substrate. Multiple cis wells may be desirable, for example, in order to enable the measurement of multiple polynucleotides on a single substrate. In some embodiments, a substrate with an array of nanopore sequencing devices comprises one common cis electrode, one common trans electrode, one common cis well, one common trans well, and a plurality of nanopore sequencing devices, such as those shown in FIG. 6 where each nanopore sequencing device comprises a FET sensor and a dual pore with a first nanopore and a second nanopore. Each nanopore sequencing device of the plurality of nanopore sequencing devices can separately measure the resistance or signal by its associated FET sensor. In other embodiments, each nanopore sequencing device may comprise a multiple pore with three or more nanopores and a FET sensor. In other embodiments, the substrate with an array of nanopore sequencing devices comprises one common cis well, a plurality of trans wells, and a plurality of nanopore sequencing devices, where each nanopore sequencing device can be individually addressable with individual trans electrodes. In other embodiments, the substrate with an array of nanopore sequencing devices comprises a plurality of cis wells, a plurality of trans wells, and a plurality of nanopore sequencing devices, where each nanopore sequencing device can be individually addressable with individual trans electrodes.

In one example, the cis electrode 30E and the trans electrode 34E are at least substantially parallel to one another in an at least substantially horizontal direction. In other examples, the cis electrode and the trans electrode may be in any suitable orientation relative to each other and to the nanopore device. The nanopore device 10D further includes a field effect transistor (FET) sensor 22E positioned between the first nanoscale opening 23E and the porous structure 2500E. The FET sensor includes a source (S) 50E, a drain (D) 52E. Metallic interconnects 66E and 64E are in electrical communication with the source 50E and drain 52E of the FET 22E, through the etch stop layer 38E. The metallic interconnects 66E and 64E communicate data from the FET sensor 22E to a control system monitoring the FET sensor 22E.

The FET sensor 22E is modified such that the FET further includes a stack of channels 601 that are aligned substantially horizontally and connect the source 50E to the drain 52E. In the example of the nanopore device 10E shown in FIG. 5E, a thin layer of gate oxide 56E is grown around the stack of channels 601. The thin layer of gate oxide separates the channels from the electrolyte 20E and exposes the channels of the FET sensor 22E to the electrolyte 20E. The thickness of the gate oxide 56E may be between about 1 and about 10 nm, and in some examples between about 2 and about 4 nm. The thickness of the gate oxide 56E is chosen such that a strong enough electric field, given the potential $V_M$, can induce an inversion layer of electrons or holes which constitutes a conductive path at the channel 54E-gate oxide 56E boundary to conduct between the source 50E and drain 52E. Each channel 605 of the plurality of channels therefore has an upper surface 607 and a lower surface 608 of the gate oxide fluidically connecting to the middle well 15E. Each channel 605 may have a vertical surface fluidically connecting to the fluidic tunnel 21E. The fluidic tunnel 21E extends through each of the plurality of channels. Therefore, the total FET sensing area can be increased by increasing the number of channels in the stack. By increasing the area of the channels 601 exposed to the electrolyte 20E, the potential $V_M$ has a better gate controllability over the channels. This configuration greatly increases the sensing area of the FET exposed to $\delta V_M$ and improves the LoD.

The device 10E in FIG. 6 includes a porous structure 2500E, e.g., a nanoporous frit or membrane. However, it should be realized that this example may also use a second nanoscale opening, similar to the structure in FIG. 2A. However, in the example shown in FIG. 6, the structure and function of the frit is similar to that of glass frits used in reference electrodes. The porosity of the frit is selected so that it is sufficient to establish electrical continuity across the frit (i.e., big enough to allow ionic species from the electrolyte to pass), but small enough that diffusion of polymers across it is not possible. The resistance of typical frits 1 mm² in size is on the order of 1 MΩ, therefore a 100 nm×100 nm frit may be expected to have a resistance of >1 TO. Typical frits have pore sizes of about a few nm and thickness of about 1 mm. Tuning the porosity and thickness of the frit should allow achieving the desired target of $R_{frit}$.

Other aspects and advantages of the disclosure will become apparent from this detailed description taken in conjunction with the accompanying drawings which illustrate, by way of example, the principles of the disclosure.

While only certain features of the examples have been illustrated and described herein, many modifications and changes will occur to those skilled in the art. It is, therefore, to be understood that the appended claims are intended to cover all such modifications and changes.

Various modification and variation of the described methods and compositions will be apparent to those skilled in the art without departing from the scope of the examples described herein. It should be understood that examples as claimed should not be unduly limited to the specific examples disclosed herein. Indeed, various modifications that are obvious to those skilled in the relevant fields are intended to be within the scope of the following claims.

Other aspects and advantages of the disclosure will become apparent from this detailed description taken in conjunction with the accompanying drawings which illustrate, by way of example, the principles of the disclosure.

While only certain features have been illustrated and described herein, many modifications and changes will occur to those skilled in the art. It is, therefore, to be understood that the appended claims are intended to cover all such modifications and changes.

Alternate Examples

Figure 7A:
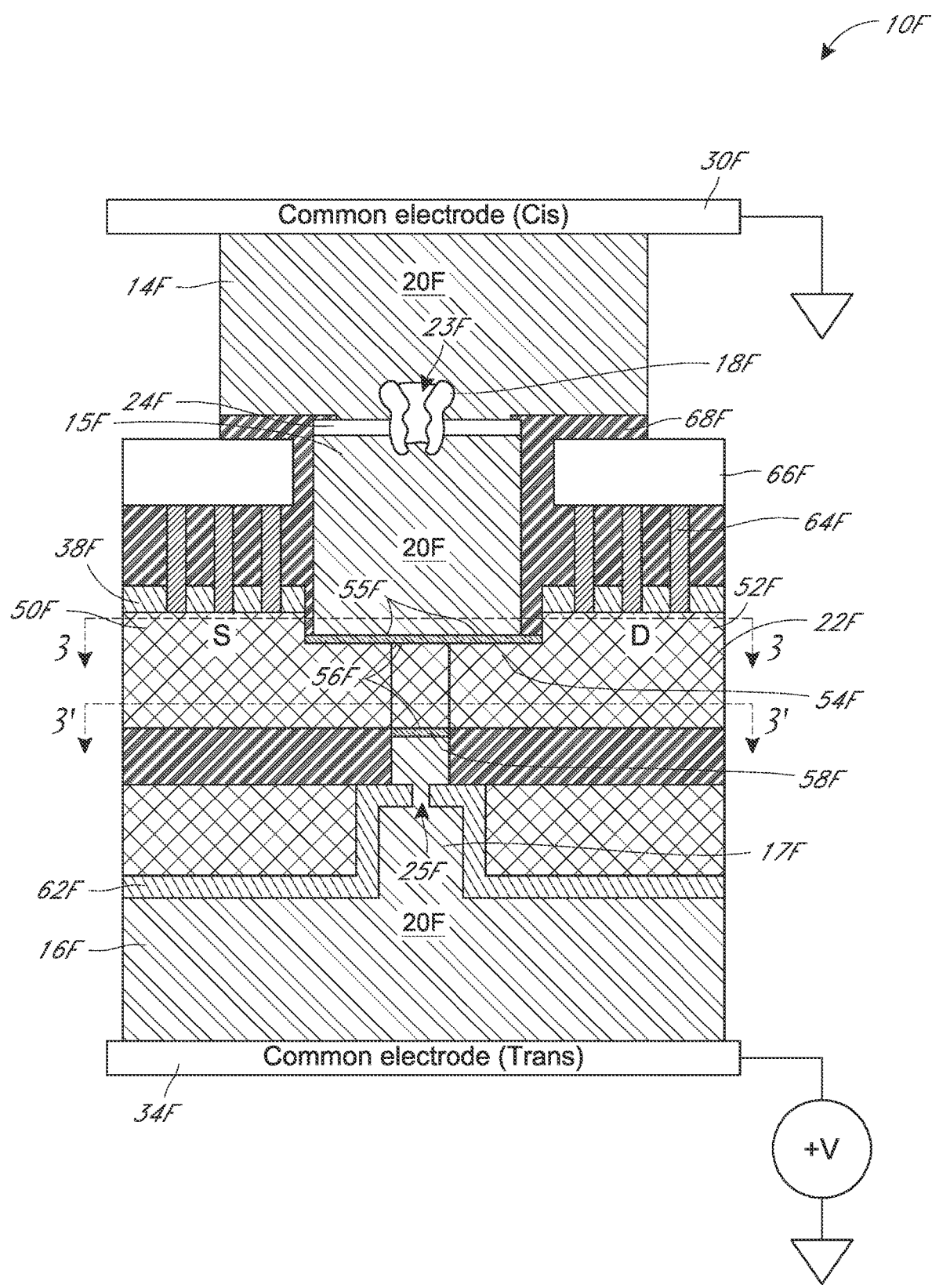
FIG. 7A is a cross-sectional side view of yet another exemplary alternate example of a nanopore sequencing device with an offset opening.
Figure 7B:
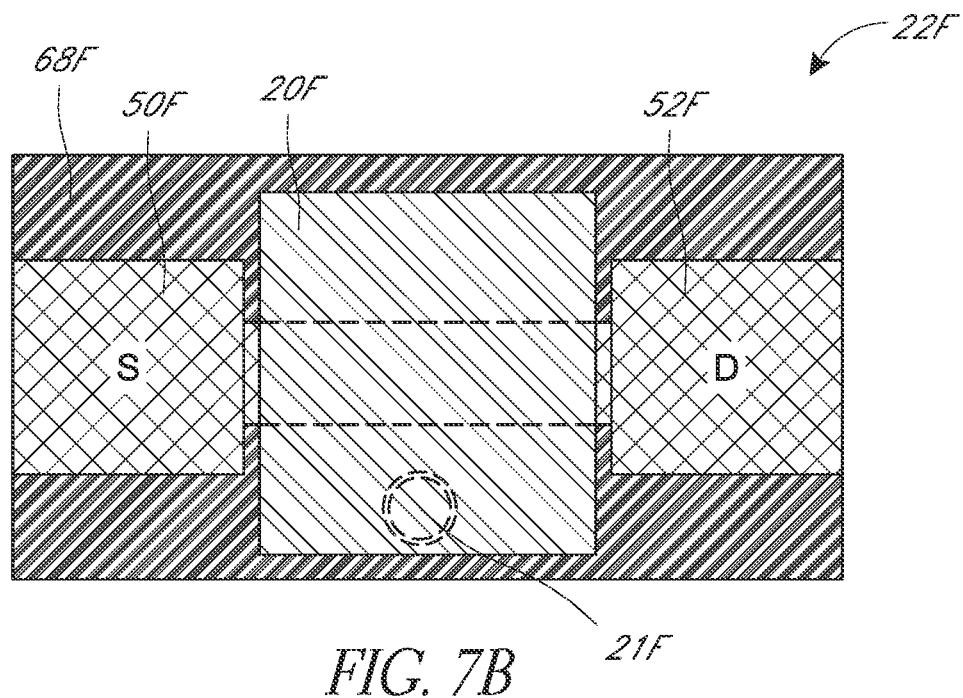
FIG. 7B is a cross-sectional top view, taken on line 3-3 of the nanopore sequencing device of FIG. 5A showing the offset opening.
Figure 7B:
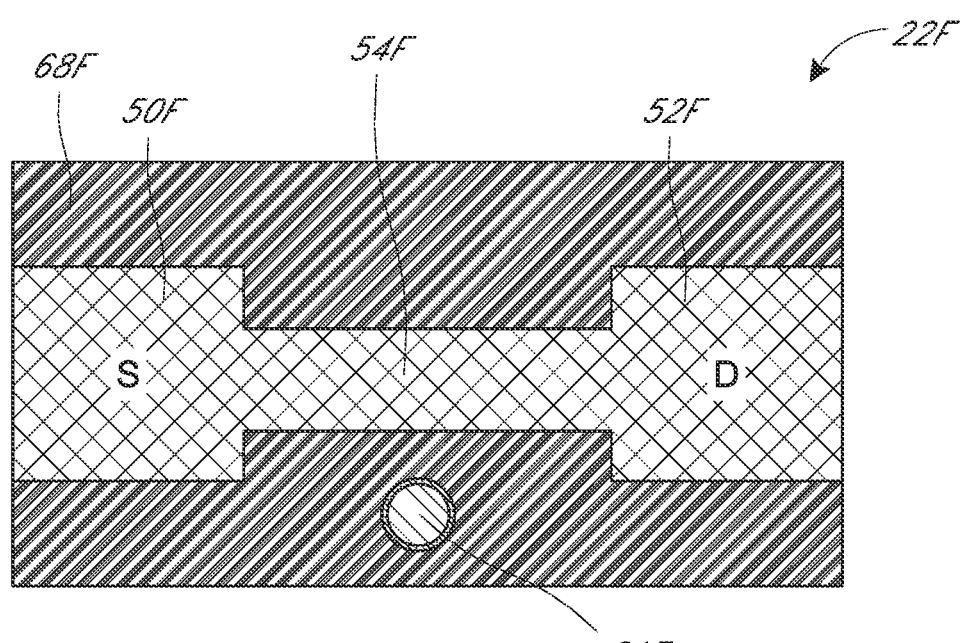

FIGS. 7A, 7B, and 7B' illustrate another variation of the nanopore device shown in FIGS. 2A, 2B, and 2B', which has an alternate arrangement of the fluidic tunnel with respect to the field effect transistor. FIG. 7A is a cross-sectional side view of a nanopore sequencing device 10F. FIG. 7B is a cross-sectional top view, taken on line 3-3 in FIG. 7A. FIG. 7B' is a cross-sectional top view, taken on line 3'-3' in FIG. 7A.

The nanopore sequencing device 10F shown in FIGS. 7A, 7B, and 7B' includes a cis electrode 30F connecting to a cis well 14F. The cis well 14F has a lower portion that includes a first nanopore 18F disposed into a membrane 24F. The first nanopore 18F includes a first nanoscale opening 23F defined by the first nanopore 18F that communicates with an offset fluidic tunnel 21F to a second nanoscale opening 25F. The second nanoscale opening 25F is disposed in a narrow region 17F between the offset fluidic tunnel 21F and a trans well 16F at a lower portion of the device 10F. As shown, the second nanoscale opening 25F is formed in the substrate material 62F. In other embodiments, the substrate material 62F does not have a narrower region, but is more planar in format, similar to the structure shown in FIG. 3A.

The first nanopore 18F provides a fluidic pathway for electrolyte 20F to pass between the cis well 14F and the middle well 15F. As shown in FIG. 7B, the fluidic tunnel 21F is located offset from the central portion of the device and provides a fluidic pathway for the electrolyte to pass from the middle well 15F, through the second nanoscale opening 25F and to the trans well 16F.

A substrate for sequencing may include an array of nanopore sequencing devices 10F. In one example of a nanopore sequencing device, the trans well is fluidically connected to the cis well by the middle well and the respective second and first nanoscale openings. In a substrate with an array of nanopore sequencing devices, there may be one common cis well and one common trans well communicating with a portion, or all, of the nanopore sequencing devices within the array on the substrate. However, it should be understood that an array of the nanopore devices may also include several cis wells that are fluidically isolated from one another and are fluidically connected to respective one or more trans wells fluidically isolated from one another and defined in the substrate. Multiple cis wells may be desirable, for example, in order to enable the measurement of multiple polynucleotides on a single substrate. In some embodiments, a substrate with an array of nanopore sequencing devices comprises one common cis electrode, one common trans electrode, one common cis well, one common trans well, and a plurality of nanopore sequencing devices, such as those shown in FIG. 7A where each nanopore sequencing device comprises a FET sensor and a dual pore with a first nanopore and a second nanopore. Each nanopore sequencing device of the plurality of nanopore sequencing devices can separately measure the resistance or signal by its associated FET sensor. In other embodiments, each nanopore sequencing device may comprise a multiple pore with three or more nanopores and a FET sensor. In other embodiments, the substrate with an array of nanopore sequencing devices comprises one common cis well, a plurality of trans wells, and a plurality of nanopore sequencing devices, where each nanopore sequencing device can be individually addressable with individual trans electrodes. In other embodiments, the substrate with an array of nanopore sequencing devices comprises a plurality of cis wells, a plurality of trans wells, and a plurality of nanopore sequencing devices, where each nanopore sequencing device can be individually addressable with individual trans electrodes.

In one example, the cis electrode 30F and the trans electrode 34F are at least substantially parallel to one another in an at least substantially horizontal direction. In other examples, the cis electrode and the trans electrode may be in any suitable orientation relative to each other and to the nanopore device. The nanopore device 10F further includes a field effect transistor (FET) sensor 22F positioned between the first nanoscale opening 23F and the second nanoscale opening 25F. The FET sensor includes a source (S) 50F, a drain (D) 52F, and a channel 54F that connects the source 50F to the drain 52F. In some embodiments, the channel 54F has a nanowire configuration, similar to the structure shown in FIGS. 3B and 3C. In other embodiments, the channel 54F has a nanosheet configuration, similar to the structure shown in FIGS. 3D and 3E. Metallic interconnects 66F and 64F are in electrical communication with the source 50F and drain 52F of the FET 22F, through the etch stop layer 38F. The metallic interconnects communicate data from the FET sensor 22F to a control system monitoring the FET sensor 22F. In alternative embodiments, the nanopore sequencing device 10F may use a porous structure in lieu of the second nanoscale opening 25F, similar to the structure illustrated in FIG. 5A.

As shown in the cross-sectional top views FIGS. 7B and 7B', the fluidic tunnel 21F is offset from the channel 54F. In other words, the fluidic tunnel 21F does not extend through the channel 54F, and therefore is not seen in the cross-sectional side view FIG. 7A. Rather, the fluidic tunnel 21F extends through the interlayer dielectric 68F around the channel 54F. In FIGS. 7B and 7B', the electrolyte 20F can be seen in the fluidic tunnel 21F. The boundary of the fluidic tunnel 21F may be circular shaped as shown in FIGS. 7B and 7B'. In other embodiments, the boundary of the fluidic tunnel 21F may be oblong shaped as shown in FIG. 3D and FIG. 3E. Alternatively, the boundary of the fluidic tunnel 21F can be of nearly arbitrary shape and size. In some embodiments, the FET sensor 22F may include a stack of channels, similar to the structure illustrated in FIG. 6, but the fluidic tunnel does not extend through the stack of channels.

One non-limiting benefit of the arrangement of the offset fluidic tunnel 21F with respect to the channel 54F shown in FIGS. 7A, 7B and 7B' is a simpler fabrication process flow. Etching a hole/opening in the channel may disturb the gate oxide of the device and require an additional oxide regrowth step. The embodiment as show in FIGS. 7A, 7B and 7B' can avoid etching a hole or opening within the source-drain channel.

The interlayer dielectric 68F may be any suitable insulator, such as $SiO_2$, $HfO_2$ or $Al_2O_3$. When the interlayer dielectric 68F is silicon dioxide, etching may be performed to etch the various components of the nanopore sequencing device. For example, etching may be performed using an etchant with high anisotropy, such as fluorinated reactive ion etch including $CHF_3/O_2$, $C_2F_6$, $C_3F_8$, and $C_5F_8/CO/O_2/Ar$ as some non-limiting examples.

In one example, the source, drain, and channel of the FET sensor 22F may be formed of silicon, and a surface of the silicon may be thermally oxidized to form a gate oxide on the channel of the FET sensor 22F.

In the nanopore sequencing device 10F shown in FIG. 7A, the bulk of the material right above line 3-3 separating the channel 54F from the electrolyte 20F is removed, exposing the channel 54F of the FET sensor 22F to the electrolyte 20F. As shown in FIG. 7A, a portion the channel 54F is exposed to the electrolyte from below. In other embodiments, similar to the structure shown in FIG. 4A, the bulk of the material right below the channel 54F may be removed, or hollowed out, exposing a larger portion the channel 54F to the electrolyte from below—this may be formed by undercutting the active area 54F of the FET sensor 22F by well-known methods. Only a thin layer of gate oxide 56F is grown around the channel 54F. An upper surface 55F and a lower surface 58F of the gate oxide 56F are fluidically exposed to the electrolyte 20F in the middle well 15F. The thin layer of gate oxide 56F separates the channel 54F from the electrolyte 20F and exposes the channel 54F of the FET sensor 22F to the electrolyte 20F. The thickness of the gate oxide 56F may be between about 1 and about 10 nm, and in some examples between about 2 and about 4 nm. The thickness of the gate oxide 56F is chosen such that a strong enough electric field, given the potential $V_M$, can induce an inversion layer of electrons or holes which constitutes a conductive path at the channel 54F-gate oxide 56F boundary to conduct between the source 50F and drain 52F.

The membrane 24F may be any of the non-permeable or semi-permeable materials. The first nanoscale opening 23F extends through the membrane 24F. It is to be understood that the membrane 24F may be formed from any suitable natural or synthetic material, as described herein. In an example, the membrane 24F is selected from the group consisting of a lipid and a biomimetic equivalent of a lipid. In a further example, the membrane 24F is a synthetic membrane (e.g., a solid-state membrane, one example of which is silicon nitride), and the first nanoscale opening 23F is in a solid-state nanopore extending through the membrane 24F. In an example, the first nanoscale opening 23F extends through, for example: a polynucleotide nanopore; a polypeptide nanopore; or a solid-state nanopore, e.g., a carbon nanotube, disposed in the membrane.

The first nanopore 18F may be any of the biological nanopores, solid-state nanopores, hybrid nanopores, and synthetic nanopores. In some examples, the first nanopore 18F has two open ends and a hollow core or hole (i.e., the first nanoscale opening 23F) that connects the two open ends. When inserted into the membrane 24F, one of the open ends of the first nanopore 18F faces the cis well 14F and the other of the open ends of the first nanopore 18F faces the middle well 15F. In some instances, the open end of the first nanopore 18F that faces the middle well 15F is fluidically connected to the fluidic tunnel 21F and may also be aligned with at least a portion of the offset fluidic tunnel 21F. In other instances, the open end of the first nanopore 18F that faces the middle well 15F is fluidically connected to the fluidic tunnel 21F, but is not aligned with the offset fluidic tunnel 21F. The hollow core of the first nanopore 18F enables the fluidic and electrical connection between the cis well 14F and the middle well 15F. The diameter of the hollow core of the first nanopore 18F may range from about 1 nm up to about 1 µm, and may vary along the length of the first nanopore 18F. In some examples, the open end that faces the cis well 14F may be larger than the open end that faces the middle well 15F. In other examples, the open end that faces the cis well 14F may be smaller than the open end that faces the middle well 15F.

A method of using the nanopore sequencing device 10F may include introducing an electrolyte 20F into each of the cis well 14F, the trans well 16F, the middle well 15F and the fluidic tunnel 21F. After introducing the electrolyte, the method may include providing a polynucleotide to be sequenced into the cis well 14F. After providing the polynucleotide, the method may include applying a voltage bias between the cis electrode 30F and the trans electrode 34F. The voltage bias drives the polynucleotide from the cis well 14F to the middle well 15F, through the first nanoscale opening 23F. As the polynucleotide passes through the first nanoscale opening 23F, the electrical resistance of the first nanoscale opening varies in response to an identity of bases in the polynucleotide at the first nanoscale opening. As a result, the potential ($V_M$) of the electrolyte 20F in the middle well 15F (or equivalently, the offset fluidic tunnel 21F) varies with the identity of bases. The potential ($V_M$) is effectively the gate voltage applied to the FET, which modulates the conductivity of the channel 54F. Therefore, measurements of the response of the FET can determine the identity of the bases.

FIG. 8 illustrates yet another variation of a nanopore device, which utilizes a vertical field effect transistor such that the source-drain channel may not be etched to form a fluidic tunnel but instead is oriented vertically along a side of the fluidic path through the device as explained below. FIG. 8 is a cross-sectional side view of a vertical FET nanopore sequencing device 810G.

The nanopore sequencing device 810G shown in FIG. 8 includes a cis electrode 830G connecting to a cis well 814G. The cis well 814G has a lower portion that includes a first nanopore 818G disposed into a membrane 824G. The first nanopore 818G includes a first nanoscale opening 823G defined by the first nanopore 818G that fluidically communicates with a second nanoscale opening 825G. The second nanoscale opening 825G may be disposed in a narrower region 817G of a trans well 816G at a lower portion of the device 810G. As shown, the second nanoscale opening is formed in the substrate material 862G. In other embodiments, the substrate material 862G does not have a narrower region, but is more planar in format, similar to the structure shown in FIG. 3A. The first nanopore 818G provides a fluidic pathway for electrolyte 820G to pass between the cis well 814G and the middle well 815G. A substrate for sequencing may include an array of nanopore sequencing devices. In one example of a nanopore sequencing device, the trans well is fluidically connected to the cis well by the middle well and the respective second and first nanoscale openings. In a substrate with an array of nanopore sequencing devices, there may be one common cis well and one common trans well communicating with a portion, or all, of the nanopore sequencing devices within the array on the substrate. However, it should be understood that an array of the nanopore devices may also include several cis wells that are fluidically isolated from one another and are fluidically connected to respective one or more trans wells fluidically isolated from one another and defined in the substrate. Multiple cis wells may be desirable, for example, in order to enable the measurement of multiple polynucleotides on a single substrate. In some embodiments, a substrate with an array of nanopore sequencing devices comprises one common cis electrode, one common trans electrode, one common cis well, one common trans well, and a plurality of nanopore sequencing devices, such as those shown in FIG. 8 where each nanopore sequencing device comprises a FET sensor and a dual pore with a first nanopore and a second nanopore. Each nanopore sequencing device of the plurality of nanopore sequencing devices can separately measure the resistance or signal by its associated FET sensor. In other embodiments, each nanopore sequencing device may comprise a multiple pore with three or more nanopores and a FET sensor. In other embodiments, the substrate with an array of nanopore sequencing devices comprises one common cis well, a plurality of trans wells, and a plurality of nanopore sequencing devices, where each nanopore sequencing device can be individually addressable with individual trans electrodes. In other embodiments, the substrate with an array of nanopore sequencing devices comprises a plurality of cis wells, a plurality of trans wells, and a plurality of nanopore sequencing devices, where each nanopore sequencing device can be individually addressable with individual trans electrodes.

In one example, the cis electrode 830G and the trans electrode 834G are at least substantially parallel to one another in an at least substantially horizontal direction. In other examples, the cis electrode and the trans electrode may be in any suitable orientation relative to each other and to the nanopore device. The nanopore device 810G further includes a vertical field effect transistor (FET) sensor positioned between the first nanoscale opening 823G and the second nanoscale opening 825G. The FET sensor includes a source (SRC) 850G, a drain (DRN) 852G, and a channel that connects the source to the drain. The FET channel is along the vertical direction, which is the direction from the cis electrode 830G to the trans electrode 834G. In some embodiments, the channel has a nanowire configuration, similar to the structure shown in FIGS. 3B and 3C. In other embodiments, the channel has a nanosheet configuration, similar to the structure shown in FIGS. 3D and 3E. Metallic interconnects 866G and 864G are in electrical communication with the source 850G and drain 852G of the FET. The metallic interconnects communicate data from the FET sensor to a control system monitoring the FET sensor. In alternative embodiments, the nanopore sequencing device 810G may use a porous structure in lieu of the second nanoscale opening 825G, similar to the structure illustrated in FIG. 5A.

As shown in FIG. 8, the source 850G, channel, and drain 852G of the vertical FET sensor are vertically stacked. The vertical FET is arranged on a lateral side of the middle well 815G. In one example, the source, drain, and channel of the FET sensor may be formed of silicon, and a surface of the silicon may be thermally oxidized to form a gate oxide 856G on the channel of the FET sensor. A vertical side surface of the gate oxide 856G is fluidically exposed to the electrolyte 820G in the middle well 815G. The thin layer of gate oxide 856G separates the channel from the electrolyte 820G and exposes the channel of the FET sensor to the electrolyte 820G. The thickness of the gate oxide 856G may be between about 1 and about 10 nm, and in some examples between about 2 and about 4 nm. The thickness of the gate oxide 856G is chosen such that a strong enough electric field, given the potential $V_M$, can induce an inversion layer of electrons or holes which constitutes a conductive path at the channel-gate oxide boundary to conduct between the source 850G and drain 852G. In some embodiments, the FET sensor may include a plurality of vertical source-drain channels that are arranged in parallel along a lateral side of the middle well.

One non-limiting benefit of the vertical FET sensor is that etching of a fluidic tunnel through the FET channel may not be required. Etching a hole/opening in the channel may disturb the gate oxide of the device and require an additional oxide regrowth step. The embodiment as show in FIG. 8 with the vertical FET arranged on a lateral side of the middle well 815G can avoid etching a hole or opening within the source-drain channel.

The interlayer dielectric 868G may be any suitable insulator, such as $SiO_2$, $HfO_2$ or $Al_2O_3$. When the interlayer dielectric 868G is silicon dioxide, etching may be performed to etch the various components of the nanopore sequencing device. For example, etching may be performed using an etchant with high anisotropy, such as fluorinated reactive ion etch including $CHF_3/O_2$, $C_2F_6$, $C_3F_8$, and $C_5F_8/CO/O_2/Ar$ as some non-limiting examples.

The membrane 824G may be any of the non-permeable or semi-permeable materials. The first nanoscale opening 823G extends through the membrane 824G. It is to be understood that the membrane 824G may be formed from any suitable natural or synthetic material, as described herein. In an example, the membrane 824G is selected from the group consisting of a lipid and a biomimetic equivalent of a lipid.

In a further example, the membrane 824G is a synthetic membrane (e.g., a solid-state membrane, one example of which is silicon nitride), and the first nanoscale opening 823G is in a solid-state nanopore extending through the membrane 824G. In an example, the first nanoscale opening 823G extends through, for example: a polynucleotide nanopore; a polypeptide nanopore; or a solid-state nanopore, e.g., a carbon nanotube, disposed in the membrane.

The first nanopore 818G may be any of the biological nanopores, solid-state nanopores, hybrid nanopores, and synthetic nanopores. In some examples, the first nanopore 818G has two open ends and a hollow core or hole (i.e., the first nanoscale opening 823G) that connects the two open ends. When inserted into the membrane 824G, one of the open ends of the first nanopore 818G faces the cis well 814G and the other of the open ends of the first nanopore 818G faces the middle well 815G. The hollow core of the first nanopore 818G enables the fluidic and electrical connection between the cis well 814G and the middle well 815G. The diameter of the hollow core of the first nanopore 818G may range from about 1 nm up to about 1 μm, and may vary along the length of the first nanopore 818G. In some examples, the open end that faces the cis well 814G may be larger than the open end that faces the middle well 815G. In other examples, the open end that faces the cis well 814G may be smaller than the open end that faces the middle well 815G.

A method of using the nanopore sequencing device 810G may include introducing an electrolyte 820G into each of the cis well 814G, the trans well 816G, and the middle well 815G. After introducing the electrolyte, the method may include providing a polynucleotide to be sequenced into the cis well 814G. After providing the polynucleotide, the method may include applying a voltage bias between the cis electrode 830G and the trans electrode 834G. The voltage bias drives the polynucleotide from the cis well 814G to the middle well 815G, through the first nanoscale opening 823G. As the polynucleotide passes through the first nanoscale opening 823G, the electrical resistance of the first nanoscale opening varies in response to an identity of bases in the polynucleotide at the first nanoscale opening. As a result, the potential ($V_M$) of the electrolyte 820G in the middle well 815G varies with the identity of bases. The potential ($V_M$) is effectively the gate voltage applied to the FET, which modulates the conductivity of the FET channel. Therefore, measurements of the response of the FET can determine the identity of the bases.

FIG. 9 illustrates yet another further variation of a nanopore sequencing device with a field effect transistor (FET) having a non-Faradaic metal electrode. In this embodiment, the FET has a non-Faradaic metal electrode, which includes a metal structure that does not participate in the Faradaic processes in the nanopore sequencing device, i.e., no electrochemical reaction occurs at the metal structure. The non-Faradaic metal electrode is used to detect the electrical potential of the electrolyte in the middle well and to transmit the potential as a detected signal to the FET. This design means that the FET can detect the potential of the electrolyte but not be exposed to the electrolyte. FIG. 9 is a cross-sectional side view of a nanopore sequencing device 910H.

The nanopore sequencing device 910H shown in FIG. 9 includes a cis electrode 930H connecting to a cis well 914H. The cis well 914H has a lower portion that includes a first nanopore 918H disposed into a membrane 924H. The first nanopore 918H includes a first nanoscale opening 923H defined by the first nanopore 918H that fluidically communicates with a second nanoscale opening 925H. The second nanoscale opening 925H may be disposed in a narrower region 917H of a trans well 916H at a lower portion of the device 910H. As shown, the second nanoscale opening is formed in the substrate material 962H. In other embodiments, the substrate material 962H does not have a narrower region, but is more planar in format, similar to the structure shown in FIG. 3A. The first nanopore 918H provides a fluidic pathway for electrolyte 920H to pass between the cis well 914H and the middle well 915H.

In one example, the cis electrode 930H and the trans electrode 934H are at least substantially parallel to one another in an at least substantially horizontal direction. In other examples, the cis electrode and the trans electrode may be in any suitable orientation relative to each other and to the nanopore device. The nanopore device 910H further includes a field effect transistor (FET) sensor 922H positioned between the first nanoscale opening 923H and the second nanoscale opening 925H. The FET sensor 922H includes a source (SRC) 950H, a drain (DRN) 952H, and a channel 954H that connects the source 950H to the drain 952H. The FET channel may be along the horizontal direction. In some embodiments, the FET channel has a nanowire configuration, similar to the structure shown in FIGS. 3B and 3C. In other embodiments, the FET channel has a nanosheet configuration, similar to the structure shown in FIGS. 3D and 3E. Metallic interconnects 966H and 964H are in electrical communication with the source 950H and drain 952H of the FET. The metallic interconnects 966H and 964H communicate data from the FET sensor to a control system (now shown) that is monitoring the FET sensor. In alternative embodiments, the nanopore sequencing device 910H may use a porous structure in lieu of the second nanoscale opening 925H, similar to the structure illustrated in FIG. 5A.

As shown in FIG. 9, the FET sensor 922H is not in direct contact with the electrolyte. In one example, the source, drain, and channel of the FET sensor may be formed of silicon, and a surface of the silicon may be thermally oxidized to form a gate oxide 956H on the channel of the FET sensor. As shown in FIG. 9, the gate oxide 956H is not fluidically exposed to the electrolyte 920H in the middle well 915H. Instead, a non-Faradaic metal electrode structure 999H is exposed to the electrolyte. The metal structure 999H is used to detect the potential $V_M$ of the electrolyte in the middle well and to transmit the detected signal to the FET. Compared to the size of the middle well which is of the order of a few μm, the path length or a characteristic size of the metal structure 999H may be about 1 μm, 2 μm, 3 μm, 4 μm, 5 μm, 6 μm, 7 μm, 8 μm, 9 μm, 10 μm, 20 μm, 30 μm, 40 μm, 50 μm, 60 μm, 70 μm, 80 μm, 90 μm, 100 μm, 110 μm, 120 μm, 130 μm, 140 μm, 150 μm, 160 μm, 170 μm, 180 μm, 190 μm, 200 μm, 210 μm, 220 μm, 230 μm, 240 μm, 250 μm, 260 μm, 270 μm, 280 μm, 290 μm, 300 μm, or any value therebetween.

The size and shape of the metal structure 999H may be chosen appropriately to avoid a high parasitic capacitance in the system. The metal structure 999H may be made of non-Faradaic corrosion-resistant metals with respect to the electrolyte. The metal structure 999H may be made of platinum, iridium, ruthenium, palladium, tantalum, gold, or any combination thereof. No electrochemical reaction may occur at the metal structure. In some embodiments, the metal structure 999H may have a cup-shaped portion exposed to the electrolyte in order to increase the contact area with the electrolyte. In some embodiments, the portion of the metal structure 999H exposed to the electrolyte may include one or more holes or openings. In some embodiments, the portion of the metal structure 999H exposed to the electrolyte may include several parallel fins in order to increase the contact area with the electrolyte, where the fins may be partially vertically or horizontally arranged. Using the metal structure 999H to contact the electrolyte allows the FET to be decoupled from the middle well, which may be easier to manufacture in some embodiments. Decoupling the size of the FET with the size of the middle well also allows a larger FET, which may allow a higher signal detection sensitivity and a lower noise level. This configuration also allows decoupling of the size of the FET, which determines the limit of signal detection, from the size of the metal structure 999H, and thus provides more design flexibility.

The thickness of the gate oxide 956H may be between about 1 and about 10 nm, and in some examples between about 2 and about 4 nm. The thickness of the gate oxide 956H is chosen such that a strong enough electric field, given the potential $V_M$ in the middle well, can induce an inversion layer of electrons or holes which constitutes a conductive path at the channel-gate oxide boundary to conduct between the source 950H and drain 952H. The interlayer dielectric 968H may be any suitable insulator, such as $SiO_2$, $HfO_2$ or $Al_2O_3$. When the interlayer dielectric 968H is silicon dioxide, etching may be performed to etch the various components of the nanopore sequencing device. For example, etching may be performed using an etchant with high anisotropy, such as fluorinated reactive ion etch including $CHF_3/O_2$, $C_2F_5$, $C_3F_8$, and $C_5F_8/CO/O_2/Ar$ as some non-limiting examples.

The membrane 924H may be any of the non-permeable or semi-permeable materials. The first nanoscale opening 923H extends through the membrane 924H. It is to be understood that the membrane 924H may be formed from any suitable natural or synthetic material, as described herein. In an example, the membrane 924H is selected from the group consisting of a lipid and a biomimetic equivalent of a lipid. In a further example, the membrane 924H is a synthetic membrane (e.g., a solid-state membrane, one example of which is silicon nitride), and the first nanoscale opening 923H is in a solid-state nanopore extending through the membrane 924H. In an example, the first nanoscale opening 923H extends through, for example: a polynucleotide nanopore; a polypeptide nanopore; or a solid-state nanopore, e.g., a carbon nanotube, disposed in the membrane. The first nanopore 918H may be any of the biological nanopores, solid-state nanopores, hybrid nanopores, and synthetic nanopores. In some examples, the first nanopore 918H has two open ends and a hollow core or hole (i.e., the first nanoscale opening 923H) that connects the two open ends. When inserted into the membrane 924H, one of the open ends of the first nanopore 918H faces the cis well 914H and the other of the open ends of the first nanopore 918H faces the middle well 915H. The hollow core of the first nanopore 918H enables the fluidic and electrical connection between the cis well 914H and the middle well 915H. The diameter of the hollow core of the first nanopore 918H may range from about 1 nm up to about 1 μm, and may vary along the length of the first nanopore 918H. In some examples, the open end that faces the cis well 914H may be larger than the open end that faces the middle well 915H. In other examples, the open end that faces the cis well 914H may be smaller than the open end that faces the middle well 915H.

A method of using the nanopore sequencing device 910H may include introducing an electrolyte 920H into each of the cis well 914H, the trans well 916H, and the middle well 915H. After introducing the electrolyte, the method may include providing a polynucleotide to be sequenced into the cis well 914H. After providing the polynucleotide, the method may include applying a voltage bias between the cis electrode 930H and the trans electrode 934H. In some embodiments, the voltage bias may drive the polynucleotide from the cis well 914H to the middle well 915H, through the first nanoscale opening 923H. As the polynucleotide passes through the first nanoscale opening 923H, the electrical resistance of the first nanoscale opening varies in response to an identity of bases in the polynucleotide at the first nanoscale opening. In alternative embodiments, the polynucleotide does not pass through the first nanoscale opening, but tags or labels of nucleotides being incorporated by a polymerase acting on the polynucleotide may pass through the first nanoscale opening or may temporarily reside in the first nanoscale opening. Thus, the electrical resistance of the first nanoscale opening varies in response to an identity of the nucleotide being incorporated, which is complementary to the identity of a base in the polynucleotide. As a result, the potential ($V_M$) of the electrolyte 920H in the middle well 915H varies with the identities of bases in the polynucleotide. The potential ($V_M$) is effectively the gate voltage applied to the FET, which modulates the conductivity of the FET channel. Therefore, measurements of the response of the FET can determine the identity of the bases in the polynucleotide.

A substrate for sequencing may include an array of nanopore sequencing devices such as those shown in FIG. 9. In one example of a nanopore sequencing device, the trans well is fluidically connected to the cis well by the middle well and the respective second and first nanoscale openings. In a substrate with an array of nanopore sequencing devices, there may be one common cis well and one common trans well communicating with a portion, or all, of the nanopore sequencing devices within the array on the substrate. However, it should be understood that an array of the nanopore devices may also include several cis wells that are fluidically isolated from one another and are fluidically connected to respective one or more trans wells fluidically isolated from one another and defined in the substrate. Multiple cis wells may be desirable, for example, in order to enable the measurement of multiple polynucleotides on a single substrate. In some embodiments, a substrate with an array of nanopore sequencing devices comprises one common cis electrode, one common trans electrode, one common cis well, one common trans well, and a plurality of nanopore sequencing devices, such as those shown in FIG. 9 where each nanopore sequencing device comprises a FET sensor and a dual pore with a first nanopore and a second nanopore. Each nanopore sequencing device of the plurality of nanopore sequencing devices can separately measure the resistance or signal by its associated FET sensor. In other embodiments, each nanopore sequencing device may comprise a multiple pore with three or more nanopores and a FET sensor. In other embodiments, the substrate with an array of nanopore sequencing devices comprises one common cis well, a plurality of trans wells, and a plurality of nanopore sequencing devices, where each nanopore sequencing device can be individually addressable with individual trans electrodes. In other embodiments, the substrate with an array of nanopore sequencing devices comprises a plurality of cis wells, a plurality of trans wells, and a plurality of nanopore sequencing devices, where each nanopore sequencing device can be individually addressable with individual trans electrodes.

Definitions

All technical and scientific terms used herein have the same meaning as commonly understood to one of ordinary skill in the art to which this disclosure belongs unless clearly indicated otherwise.

As used herein, the singular forms "a", "and", and "the" include plural referents unless the context clearly dictates otherwise. Thus, for example, reference to "a sequence" may include a plurality of such sequences, and so forth.

The terms comprising, including, containing and various forms of these terms are synonymous with each other and are meant to be equally broad. Moreover, unless explicitly stated to the contrary, examples comprising, including, or having an element or a plurality of elements having a particular property may include additional elements, whether or not the additional elements have that property.

As used herein, the terms "fluidically connecting," "fluid communication," "fluidically coupled," and the like refer to two spatial regions being connected together such that a liquid or gas may flow between the two spatial regions. For example, a cis well/wells may be fluidically connected to a trans well/wells by way of a middle well, a fluidic tunnel, and a narrower region, such that at least a portion of an electrolyte may flow between the connected wells. The two spatial regions may be in fluid communication through first and second nanoscale openings, or through one or more valves, restrictors, or other fluidic components that are to control or regulate a flow of fluid through a system.

As used herein, the term "interstitial region" refers to an area in a substrate/solid support or a membrane, or an area on a surface that separates other areas, regions, features associated with the support or membrane or surface. For example, an interstitial region of a membrane can separate one nanopore of an array from another nanopore of the array. For another example, an interstitial region of a substrate can separate one trans well from another trans well. The two areas that are separated from each other can be discrete, i.e., lacking physical contact with each other. In many examples, the interstitial region is continuous whereas the areas are discrete, for example, as is the case for a plurality of nanopores defined in an otherwise continuous membrane, or for a plurality of wells defined in an otherwise continuous substrate/support. The separation provided by an interstitial region can be partial or full separation. Interstitial regions may have a surface material that differs from the surface material of the features defined in the surface. For example, the surface material at the interstitial regions may be a lipid material, and a nanopore formed in the lipid material can have an amount or concentration of polypeptide that exceeds the amount or concentration present at the interstitial regions. In some examples, the polypeptide may not be present at the interstitial regions.

As used herein, the term "membrane" refers to a non-permeable or semi-permeable barrier or other sheet that separates two liquid/gel chambers (e.g., a cis well and a fluidic cavity) which can contain the same compositions or different compositions therein. The permeability of the membrane to any given species depends upon the nature of the membrane. In some examples, the membrane may be non-permeable to ions, to electric current, and/or to fluids. For example, a lipid membrane may be impermeable to ions (i.e., does not allow any ion transport therethrough), but may be at least partially permeable to water (e.g., water diffusivity ranges from about 40 μm/s to about 100 μm/s). For another example, a synthetic/solid-state membrane, one example of which is silicon nitride, may be impermeable to ions, electric charge, and fluids (i.e., the diffusion of all of these species is zero). Any membrane may be used in accordance with the present disclosure, as long as the membrane can include a transmembrane nanoscale opening and can maintain a potential difference across the membrane. The membrane may be a monolayer or a multilayer membrane. A multilayer membrane includes two or more layers, each of which is a non-permeable or semi-permeable material.

The membrane may be formed of materials of biological or non-biological origin. A material that is of biological origin refers to material derived from or isolated from a biological environment such as an organism or cell, or a synthetically manufactured version of a biologically available structure (e.g., a biomimetic material).

An example membrane that is made from the material of biological origin includes a monolayer formed by a bola-lipid. Another example membrane that is made from the material of biological origin includes a lipid bilayer. Suitable lipid bilayers include, for example, a membrane of a cell, a membrane of an organelle, a liposome, a planar lipid bilayer, and a supported lipid bilayer. A lipid bilayer can be formed, for example, from two opposing layers of phospholipids, which are arranged such that their hydrophobic tail groups face towards each other to form a hydrophobic interior, whereas the hydrophilic head groups of the lipids face outwards towards the aqueous environment on each side of the bilayer. Lipid bilayers also can be formed, for example, by a method in which a lipid monolayer is carried on an aqueous solution/air interface past either side of an aperture that is substantially perpendicular to that interface. The lipid is normally added to the surface of an aqueous electrolyte solution by first dissolving it in an organic solvent and then allowing a drop of the solvent to evaporate on the surface of the aqueous solution on either side of the aperture. Once the organic solvent has at least partially evaporated, the solution/air interfaces on either side of the aperture are physically moved up and down past the aperture until a bilayer is formed. Other suitable methods of bilayer formation include tip-dipping, painting bilayers, and patch-clamping of liposome bilayers. Any other methods for obtaining or generating lipid bilayers may also be used.

A material that is not of biological origin may also be used as the membrane. Some of these materials are solid-state materials and can form a solid-state membrane, and others of these materials can form a thin liquid film or membrane. The solid-state membrane can be a monolayer, such as a coating or film on a supporting substrate (i.e., a solid support), or a freestanding element. The solid-state membrane can also be a composite of multilayered materials in a sandwich configuration. Any material not of biological origin may be used, as long as the resulting membrane can include a transmembrane nanoscale opening and can maintain a potential difference across the membrane. The membranes may include organic materials, inorganic materials, or both. Examples of suitable solid-state materials include, for example, microelectronic materials, insulating materials (e.g., silicon nitride ($Si_3N_4$), aluminum oxide ($Al_2O_3$), hafnium oxide ($HfO_2$), tantalum pentoxide ($Ta_2O_5$), silicon oxide ($SiO_2$), etc.), some organic and inorganic polymers (e.g., polyamide, plastics, such as polytetrafluoroethylene (PTFE), or elastomers, such as two-component addition-cure silicone rubber), and glasses. In addition, the solid-state membrane can be made from a monolayer of graphene, which is an atomically thin sheet of carbon atoms densely packed into a two-dimensional honeycomb lattice, a multi-layer of graphene, or one or more layers of graphene mixed with one or more layers of other solid-state materials. A graphene-containing solid-state membrane can include at least one graphene layer that is a graphene nanoribbon or graphene nanogap, which can be used as an electrical sensor to characterize the target polynucleotide. It is to be understood that the solid-state membrane can be made by any suitable method, for example, chemical vapor deposition (CVD). In an example, a graphene membrane can be prepared through either CVD or exfoliation from graphite. Examples of suitable thin liquid film materials that may be used include diblock copolymers or triblock copolymers, such as amphiphilic PMOXA-PDMS-PMOXA ABA triblock copolymers.

As used herein, the term "nanopore" is intended to mean a hollow structure discrete from, or defined in, and extending across the membrane that permits ions, electric current, and/or fluids to cross from one side of the membrane to the other side of the membrane. For example, a membrane that inhibits the passage of ions or water-soluble molecules can include a nanopore structure that extends across the membrane to permit the passage (through a nanoscale opening extending through the nanopore structure) of the ions or water-soluble molecules from one side of the membrane to the other side of the membrane. The diameter of the nanoscale opening extending through the nanopore structure can vary along its length (i.e., from one side of the membrane to the other side of the membrane), but at any point is on the nanoscale (i.e., from about 1 nm to about 100 nm, or to less than 1000 nm). Examples of the nanopore include, for example, biological nanopores, solid-state nanopores, and biological and solid-state hybrid nanopores.

As used herein, the term "diameter" is intended to mean a longest straight line inscribable in a cross-section of a nanoscale opening through a centroid of the cross-section of the nanoscale opening. It is to be understood that the nanoscale opening may or may not have a circular or substantially circular cross-section (the cross-section of the nanoscale opening being substantially parallel with the cis/trans electrodes). Further, the cross-section may be regularly or irregularly shaped.

As used herein, the term "biological nanopore" is intended to mean a nanopore whose structure portion is made from materials of biological origin. Biological origin refers to a material derived from or isolated from a biological environment such as an organism or cell, or a synthetically manufactured version of a biologically available structure. Biological nanopores include, for example, polypeptide nanopores and polynucleotide nanopores.

As used herein, the term "polypeptide nanopore" is intended to mean a protein/polypeptide that extends across the membrane, and permits ions, electric current, polymers such as DNA or peptides, or other molecules of appropriate dimension and charge, and/or fluids to flow therethrough from one side of the membrane to the other side of the membrane. A polypeptide nanopore can be a monomer, a homopolymer, or a heteropolymer. Structures of polypeptide nanopores include, for example, an α-helix bundle nanopore and a β-barrel nanopore. Example polypeptide nanopores include α-hemolysin, *Myobacterium smegmatis* porin A (MspA), gramicidin A, maltoporin, OmpF, OmpC, PhoE, Tsx, F-pilus, etc. The protein α-hemolysin is found naturally in cell membranes, where it acts as a pore for ions or molecules to be transported in and out of cells. *Mycobacterium smegmatis* porin A (MspA) is a membrane porin produced by Mycobacteria, which allows hydrophilic molecules to enter the bacterium. MspA forms a tightly interconnected octamer and transmembrane beta-barrel that resembles a goblet and contains a central pore.

A polypeptide nanopore can be synthetic. A synthetic polypeptide nanopore includes a protein-like amino acid sequence that does not occur in nature. The protein-like amino acid sequence may include some of the amino acids that are known to exist but do not form the basis of proteins (i.e., non-proteinogenic amino acids). The protein-like amino acid sequence may be artificially synthesized rather than expressed in an organism and then purified/isolated.

As used herein, the term "polynucleotide nanopore" is intended to include a polynucleotide that extends across the membrane, and permits ions, electric current, and/or fluids to flow from one side of the membrane to the other side of the membrane. A polynucleotide pore can include, for example, a polynucleotide origami (e.g., nanoscale folding of DNA to create the nanopore).

Also as used herein, the term "solid-state nanopore" is intended to mean a nanopore whose structure portion is defined by a solid-state membrane and includes materials of non-biological origin (i.e., not of biological origin). A solid-state nanopore can be formed of an inorganic or organic material. Solid-state nanopores include, for example, silicon nitride nanopores, silicon dioxide nanopores, and graphene nanopores.

The nanopores disclosed herein may be hybrid nanopores. A "hybrid nanopore" refers to a nanopore including materials of both biological and non-biological origins. An example of a hybrid nanopore includes a polypeptide-solid-state hybrid nanopore and a polynucleotide-solid-state nanopore.

As used herein, the term "nanopore sequencer" refers to any of the devices disclosed herein that can be used for nanopore sequencing. In the examples disclosed herein, during nanopore sequencing, the nanopore is immersed in example(s) of the electrolyte disclosed herein and a potential difference is applied across the membrane. In an example, the potential difference is an electric potential difference or an electrochemical potential difference. An electrical potential difference can be imposed across the membrane via a voltage source that injects or administers current to at least one of the ions of the electrolyte contained in the cis well or one or more of the trans wells. An electrochemical potential difference can be established by a difference in ionic composition of the cis and trans wells in combination with an electrical potential. The different ionic composition can be, for example, different ions in each well or different concentrations of the same ions in each well.

The application of the potential difference across the nanopores may force the translocation of a nucleic acid through the first nanoscale opening 23 (shown, e.g., in FIG. 2A and described in more detail below). One or more signals are generated that correspond to the translocation of the nucleotide through the nanopore. Accordingly, as a target polynucleotide, or as a mononucleotide or a probe derived from the target polynucleotide or mononucleotide, transits through the nanopore, the current across the membrane changes due to base-dependent (or probe dependent) blockage of the constriction, for example. The signal from that change in current can be measured using any of a variety of methods. Each signal is unique to the species of nucleotide(s) (or probe) in the nanopore, such that the resultant signal can be used to determine a characteristic of the polynucleotide. For example, the identity of one or more species of nucleotide(s) (or probe) that produces a characteristic signal can be determined.

As used herein, a "nucleotide" includes a nitrogen containing heterocyclic base, a sugar, and one or more phosphate groups. Nucleotides are monomeric units of a nucleic acid sequence. Examples of nucleotides include, for example, ribonucleotides or deoxyribonucleotides. In ribonucleotides (RNA), the sugar is a ribose, and in deoxyribonucleotides (DNA), the sugar is a deoxyribose, i.e., a sugar lacking a hydroxyl group that is present at the 2' position in ribose. The nitrogen containing heterocyclic base can be a purine base or a pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine. The phosphate groups may be in the mono-, di-, or tri-phosphate form. These nucleotides are natural nucleotides, but it is to be further understood that non-natural nucleotides, modified nucleotides or analogs of the aforementioned nucleotides can also be used.

As used herein, the term "signal" is intended to mean an indicator that represents information. Signals include, for example, an electrical signal and an optical signal. The term "electrical signal" refers to an indicator of an electrical quality that represents information. The indicator can be, for example, current, voltage, tunneling, resistance, potential, voltage, conductance, or a transverse electrical effect. An "electronic current" or "electric current" refers to a flow of electric charge. In an example, an electrical signal may be an electric current passing through a nanopore, and the electric current may flow when an electric potential difference is applied across the nanopore.

The term "substrate" refers to a rigid, solid support that is insoluble in aqueous liquid and is incapable of passing a liquid absent an aperture, port, or other like liquid conduit. In the examples disclosed herein, the substrate may have wells or chambers defined therein. Examples of suitable substrates include glass and modified or functionalized glass, plastics (including acrylics, polystyrene and copolymers of styrene and other materials, polypropylene, polyethylene, polybutylene, polyurethanes, polytetrafluoroethylene (PTFE) (such as TEFLON® from Chemours), cyclic olefins/cyclo-olefin polymers (COP) (such as ZEONOR® from Zeon), polyimides, etc.), nylon, ceramics, silica or silica-based materials, silicon and modified silicon, carbon, metals, inorganic glasses, and optical fiber bundles.

The terms top, bottom, lower, upper, on, etc. are used herein to describe the device/nanopore sequencer and/or the various components of the device. It is to be understood that these directional terms are not meant to imply a specific orientation, but are used to designate relative orientation between components. The use of directional terms should not be interpreted to limit the examples disclosed herein to any specific orientation(s). As used herein, the terms "upper", "lower", "vertical", "horizontal" and the like are meant to indicate relative orientation.

As used herein, the terms "well", "cavity" and "chamber" are used synonymously, and refer to a discrete feature defined in the device that can contain a fluid (e.g., liquid, gel, gas). A cis well is a chamber that contains or is partially defined by a cis electrode, and is also fluidically connected to the fluidic system of a FET which in turn is fluidically connected to a trans well/chamber. Examples of an array of the present device may have one cis well or multiple cis wells. The trans well is a single chamber that contains or is partially defined by its own trans electrode, and is also fluidically connected to a cis well. In examples including multiple trans wells, each trans well is electrically isolated from each other trans well. Further, it is to be understood that the cross-section of a well taken parallel to a surface of a substrate at least partially defining the well can be curved, square, polygonal, hyperbolic, conical, angular, etc.

As used herein, "field-effect transistors" or "FETs" typically include doped source/drain regions that are formed of a semiconductor material, e.g., silicon, germanium, gallium arsenide, silicon carbide, etc., and are separated by a channel region. A n-FET is a FET having an n-channel in which the current carriers are electrons. A p-FET is a FET having a p-channel in which the current carriers are holes. Source/drain regions of a n-FET device may include a different material than source/drain regions of a p-FET device. In some examples, the source/drain regions or the channel may not be doped. Doped regions may be formed by adding dopant atoms to an intrinsic semiconductor. This changes the electron and hole carrier concentrations of the intrinsic semiconductor at thermal equilibrium. A doped region may be p-type or n-type. As used herein, "p-type" refers to the addition of impurities to an intrinsic semiconductor that creates a deficiency of valence electrons. For silicon, example p-type dopants, i.e., impurities, include but are not limited to boron, aluminum, gallium, and indium. As used herein, "n-type" refers to the addition of impurities that contribute free electrons to an intrinsic semiconductor. For silicon, example n-type dopants, i.e., impurities, include but are not limited to, antimony, arsenic, and phosphorus. The dopant(s) may be introduced by ion implantation or plasma doping.

For example, in an integrated circuit having a plurality of metal oxide semiconductor field effect transistors (MOSFETs), each MOSFET has a source and a drain that are formed in an active region of a semiconductor layer by implanting n-type or p-type impurities in the layer of semiconductor material. Disposed between the source and the drain is a channel (or body) region. Disposed above the body region is a gate electrode. The gate electrode and the body are spaced apart by a gate dielectric (gate oxide) layer. The channel region connects the source and the drain, and electrical current flows through the channel region from the source to the drain. The electrical current flow is induced in the channel region by a voltage applied at the gate electrode.

Non-planar transistor device architectures, such as nanosheet (or nanowire) transistors, can provide increased device density and increased performance over planar transistors. A "gate-all-around" transistor is a transistor in which the gate is structured to wrap around the channel. A "nanosheet transistor" refers to a type of FET that may include a plurality of stacked nanosheets extending between a pair of source/drain regions, forming a channel. Nanosheet transistors, in contrast to conventional planar FETs, may include a gate stack that wraps around the full perimeter of multiple nanosheet channel regions. Nanosheet transistor configurations enable fuller depletion in the nanosheet channel regions and reduce short-channel effects. "Nanowire transistors" may be similar to nanosheet transistors, except the channel may include nanowires instead of nanosheets. The gate-all-around structure in nanosheet or nanowire transistors can provide very small devices with better switching control, lower leakage current, faster operations, and lower output resistance.

A way of increasing channel conductivity and decreasing FET size is to form the channel as a nanostructure. For example, a gate-all-around (GAA) nanosheet FET is an architecture for providing a relatively small FET footprint by forming the channel region as a series of nanosheets. In a GAA configuration, a nanosheet-based FET includes a source region, a drain region and stacked nanosheet channels between the source and drain regions. A gate surrounds the stacked nanosheet channels and regulates electron flow through the nanosheet channels between the source and drain regions. GAA nanosheet FETs may be fabricated by forming alternating layers of channel nanosheets and sacrificial nanosheets. The sacrificial nanosheets are released from the channel nanosheets before the FET device is finalized. For n-type FETs, the channel nanosheets are typically silicon (Si) and the sacrificial nanosheets are typically silicon germanium (SiGe). For p-type FETs, the channel nanosheets are typically SiGe and the sacrificial nanosheets are typically Si. In some implementations, the channel nanosheet of a p-FET can be SiGe or Si, and the sacrificial nanosheets can be Si or SiGe. Forming the GAA nanosheets from alternating layers of channel nanosheets formed from a first type of semiconductor material (e.g., Si for n-type FETs, and SiGe for p-type FETs) and sacrificial nanosheets formed from a second type of semiconductor material (e.g., SiGe for n-type FETs, and Si for p-type FETs) provides superior channel electrostatics control, which is beneficial for continuously scaling gate lengths down to seven nanometer CMOS technology and below. The use of multiple layered SiGe/Si sacrificial/channel nanosheets (or Si/SiGe sacrificial/channel nanosheets) to form the channel regions in GAA FET semiconductor devices provides desirable device characteristics, including the introduction of strain at the interface between SiGe and Si.

In some examples, a "nanowire" is characterized by a critical dimension of less than about 30 nm, while a "nanosheet" is characterized by a critical dimension of about 30 nm or greater. In exemplary devices, the critical dimension is measured along the gate. In that direction, if the width of the channel is small, the channel cross-section is like a "wire" whereas if the width of the channel is large, the channel cross-section is like a "sheet."

In some examples, the smallest dimension of the nanosheet or nanowire is between about 1-10, about 1-50, about 1-100, about 1-500, or about 1-1000 nm. In some examples, the smallest dimension of the nanosheet or nanowire is between about 1-5, about 3-10, about 5-15, about 10-20, about 15-30, about 2040, about 30-50, about 40-75, about 50-100, about 75-150, about 100-200, about 150-300, about 200-400, about 300-500, about 400-750, or about 500-1000 nm. In some examples, the smallest dimension of the nanosheet is at least about 3, about 5, about 7, about 10, about 15, about 20, about 50, about 100, about 150, about 200, about 250, about 300, about 350, about 400, about 450, about 500, about 600, about 700, about 800, about 900, about 1000, about 2000, about 2500, about 3000, about 4000, or about 5000 times smaller than the other two dimensions of the nanosheet. In some examples, the smallest dimension of the nanosheet is between about 2-5, about 3-7, about 5-10, about 7-15, about 10-20, about 15-50, about 20-100, about 50-150, about 100-200, about 150-250, about 200-300, about 250-350, about 300-400, about 350-450, about 400-500, about 450-600, 5 about 00-700, about 600-800, about 700-900, about 800-1000, about 900-2000, about 1000-2500, about 2000-3000, about 2500-4000, or about 3000-5000 times smaller than the other two dimensions of the nanosheet. In some examples, the smallest dimension of the nanosheet is at most about 3, about 5, about 7, about 10, about 15, about 20, about 50, about 100, about 150, about 200, about 250, about 300, about 350, about 400, about 450, about 500, about 600, about 700, about 800, about 900, about 1000, about 2000, about 2500, about 3000, about 4000, or about 5000 times smaller than the other two dimensions of the nanosheet. In some examples, the biggest dimension of the nanowire is at least about 3, about 5, about 7, about 10, about 15, about 20, about 50, about 100, about 150, about 200, about 250, about 300, about 350, about 400, about 450, about 500, about 600, about 700, about 800, about 900, about 1000, about 2000, about 2500, about 3000, about 4000, or about 5000 times bigger than the other two dimensions of the nanowire. In some examples, the biggest dimension of the nanowire is between about 2-5, about 3-7, about 5-10, about 7-15, about 10-20, about 15-50, about 20-100, about 50-150, about 100-200, about 150-250, about 200-300, about 250-350, about 300-400, about 350-450, about 400-500, about 450-600, about 500-700, about 600-800, about 700-900, about 800-1000, about 900-2000, about 1000-2500, about 2000-3000, about 2500-4000, or about 3000-5000 times bigger than the other two dimensions of the nanowire. In some examples, the biggest dimension of the nanowire is at most about 3, about 5, about 7, about 10, about 15, about 20, about 50, about 100, about 150, about 200, about 250, about 300, about 350, about 400, about 450, about 500, about 600, about 700, about 800, about 900, about 1000, about 2000, about 2500, about 3000, about 4000, or about 5000 times bigger than the other two dimensions of the nanowire.

As used herein, a "porous structure" or "frit" refers to a body that has pore portions. The typical pore size of the pore portion may be, for example, about 100 μm or less, about 50 μm or less, about 10 μm or less, about 5 μm or less, about 1 μm or less, about 500 nm or less, about 100 nm or less, about 50 nm or less, about 10 nm or less, about 5 nm or less, about 1 nm or less, about 500 Å or less, about 100 Å or less, about 50 Å or less, about 10 Å or less, about 5 Å or less, about 100 μm or more, about 50 μm or more, about 10 μm or more, about 5 μm or more, about 1 μm or more, about 500 nm or more, about 100 nm or more, about 50 nm or more, about 10 nm or more, about 5 nm or more, about 1 nm or more, about 500 Å or more, about 100 Å or more, about 50 Å or more, about 10 Å or more, about 5 Å or more, between about 500 and about 100 μm, between about 250 and about 50 μm, between about 125 and about 25 μm, between about 50 and about 10 μm, between about 25 and about 5 μm, between about 12.5 and about 2.5 μm, between about 5.5 and about 0.5 μm, between about 500 and about 100 nm, between about 250 and about 50 nm, between about 125 and about 25 nm, between about 50 and about 10 nm, between about 25 and about 5 nm, between about 12.5 and about 2.5 nm, between about 5.5 and about 0.5 nm, between about 500 and about 100 Å, between about 250 and about 50 Å, between about 125 and about 25 Å, between about 50 and about 10 Å, between about 25 and about 5 Å, between about 12.5 and about 2.5 Å, or between about 5.5 and about 1 Å. There may be a distribution of different pore sizes.

The porous structure may be formed of a porous material comprising a matrix defining an array of pores having a porosity sufficient to enable the desired function of the porous material. As used herein, the term "porosity" refers to the amount of void space in a porous material comprising a matrix. As such, the total volume of a porous material comprising a matrix is based upon the matrix space and the void space. As used herein, the term "void space" refers to actual or physical space in a porous material comprising a matrix. As such, the total volume of a porous material comprising a matrix disclosed herein is based upon the matrix space and the void space. For example, a porous material comprising a matrix defining an array of pores may have a porosity of, e.g., about 40% of the total volume of a matrix, about 50% of the total volume of a matrix, about 60% of the total volume of a matrix, about 70% of the total volume of a matrix, about 80% of the total volume of a matrix, about 90% of the total volume of a matrix, about 95% of the total volume of a matrix, or about 97/% of the total volume of a matrix, at least about 40% of the total volume of a matrix, at least about 50% of the total volume of a matrix, at least about 60% of the total volume of a matrix, at least about 70% of the total volume of a matrix, at least about 80% of the total volume of a matrix, at least about 90% of the total volume of a matrix, at least about 95% of the total volume of a matrix, or at least about 97% of the total volume of a matrix, at most about 40% of the total volume of a matrix, at most about 50% of the total volume of a matrix, at most about 60% of the total volume of a matrix, at most about 70% of the total volume of a matrix, at most about 80% of the total volume of a matrix, at most about 90% of the total volume of a matrix, at most about 95% of the total volume of a matrix, or at most about 97% of the total volume of a matrix, about 40% to about 97% of the total volume of a matrix, about 50% to about 97% of the total volume of a matrix, about 60% to about 97% of the total volume of a matrix, about 70% to about 97% of the total volume of a matrix, about 80% to about 97% of the total volume of a matrix, about 90% to about 97% of the total volume of a matrix, about 40% to about 95% of the total volume of a matrix, about 50% to about 95% of the total volume of a matrix, about 60% to about 95% of the total volume of a matrix, about 70% to about 95% of the total volume of a matrix, about 80% to about 95% of the total volume of a matrix, about 90% to about 95% of the total volume of a matrix, about 40% to about 95% of the total volume of a matrix, about 50% to about 90% of the total volume of a matrix, about 60% to about 90% of the total volume of a matrix, about 70% to about 90% of the total volume of a matrix, or about 80% to about 90% of the total volume of a matrix. For example, a porous material comprising a matrix defining an array of pores may have a void space of, e.g., about 50% of the total volume of a matrix, about 60% of the total volume of a matrix, about 70% of the total volume of a matrix, about 80% of the total volume of a matrix, about 90% of the total volume of a matrix, about 95% of the total volume of a matrix, or about 97% of the total volume of a matrix, at least about 50% of the total volume of a matrix, at least about 60% of the total volume of a matrix, at least about 70% of the total volume of a matrix, at least about 80% of the total volume of a matrix, at least about 90% of the total volume of a matrix, at least about 95% of the total volume of a matrix, or at least about 97% of the total volume of a matrix, at most about 50% of the total volume of a matrix, at most about 60% of the total volume of a matrix, at most about 70% of the total volume of a matrix, at most about 80% of the total volume of a matrix, at most about 90% of the total volume of a matrix, at most about 95% of the total volume of a matrix, or at most 97% of the total volume of a matrix, about 50% to about 97% of the total volume of a matrix, about 60% to about 97% of the total volume of a matrix, about 70% to about 97% of the total volume of a matrix, about 80% to about 97% of the total volume of a matrix, about 90% to about 97% of the total volume of a matrix, about 50% to about 95% of the total volume of a matrix, about 60% to about 95% of the total volume of a matrix, about 70% to about 95% of the total volume of a matrix, about 80% to about 95% of the total volume of a matrix, about 90% to about 95% of the total volume of a matrix, about 50% to about 90% of the total volume of a matrix, about 60% to about 90% of the total volume of a matrix, about 70% to about 90% of the total volume of a matrix, or about 80% to about 90% of the total volume of a matrix.

The porous structure may be a porous matrix, a porous membrane, an ionomer permeable to certain types of ions, a porous glass frit, an ion-selective membrane, an ion-conductive glass, a polymer membrane, or an ion-conductive membrane. The porous structure may be formed of microporous materials such as ceramic or glass frits, ceramic or glass membranes, or solid porous substrates such as frits or wafers prepared from polymers or inorganic materials. The glass frits may contain, for example, magnesium oxide, calcium oxide, strontium oxide, barium oxide, cesium oxide, sodium oxide, potassium oxide, boron oxide, vanadium oxide, zinc oxide, tellurium oxide, aluminum oxide, silicon dioxide, lead oxide, tin oxide, phosphorus oxide, ruthenium oxide, rhodium oxide, iron oxide, copper oxide, manganese dioxide, molybdenum oxide, niobium oxide, titanium oxide, tungsten oxide, bismuth oxide, zirconium oxide, lithium oxide, antimony oxide, lead borate glass, tin phosphate glass, vanadate glass, or borosilicate glass.

In some example, the porous structure may include microporous membranes formed of polysulfone, polyethersulfone, or polyvinylidene fluoride. In some example, the porous structure may be formed of a resin material such as polyolefin such as polyethylene (PE), polyethylene terephthalate (PET), polybutylene terephthalate (PBT), polypropylene (PP), polytetrafluoroethylene (PTFE) or the like. Further, a hollow fiber membrane in a laminated structure having a non-porous film and porous films provided to hold the non-porous film in between may be used. In some example, the porous structure may be formed of PEDOT:PSS (poly(3,4-ethylenedioxythiophene) polystyrene sulfonate), silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, polysulfones and block copolymers thereof including, for example, di-block, tri-block, alternating, random and graft copolymers.

In some examples, the porous structure may be formed of a porous silicon dioxide, organosilicate glass (carbon-doped oxide), indium tin oxide (ITO), or low-κ (low dielectric constant) dielectrics including silicon carbon boron nitride (SiCBN), silicon oxycarbonitride (SiOCN), fluorine doped silicon dioxide, carbon doped silicon dioxide, diamond-like carbon (DLC) and combinations thereof. Such porous low-κ materials are commercially available for growth using chemical vapour deposition (CVD) under trade names such as Orion™ from Trikon, BDIIx™ from AMAT and Aurora™ from ASMi. Alternative materials can be deposited by being spun on—such materials include SiLK™ from Dow Chemical and LKD™ from JSR For example, a low-κ porous organosilicate glass may have a dielectric constant approximately 2.7, and a porosity (defined as the volume of pores divided by the total volume including pores and the material between the pores) greater than 10%. For example, a porous silicon dioxide may have porosity between about 15 to 40%, or between about 30 to 35%. The porous silicon dioxide may have a configuration of vertical and horizontal pores following the crystallographic orientation of the <100> silicon body. The porous silicon dioxide may be formed from a substrate material, for example based on porous silicon. In some examples, the porous structure may be formed of a porous material formed by porosification. In some examples, the porous material may be a nano-porous material that is to say with pores of size or diameter of the nanometer order. The porous material formed by porosification may be provided with pores of small diameter, for example between about 2 nm and about 100 nm. The porous material formed by porosification can be made with an open porosity greater than 30%. In some examples, the porous structure may be formed of a porous material formed by porosification of low-κ materials including, but not limited to, silicon boron nitride (SiBN), silicon carbon nitride (SiCN), silicon boron carbon nitride (SiBCN), hydrogen silsesquioxane polymer (HSQ), methyl silsesquioxane polymer (MSQ), polyphenylene oligomer, methyl doped silica or SiOx(CH3)y, SiCxOyHy or SiOCH, organosilicate glass (SiCOH), silicon oxide, boron nitride, and silicon oxynitride.

The aspects and examples set forth herein and recited in the claims can be understood in view of the above definitions.

Additional Notes

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range, as if such value or sub-range were explicitly recited. For example, a range from about 2 nm to about 20 nm should be interpreted to include not only the explicitly recited limits of from about 2 nm to about 20 nm, but also to include individual values, such as about 3.5 nm, about 8 nm, about 18.2 nm, etc., and sub-ranges, such as from about 5 nm to about 10 nm, etc. Furthermore, when "about" and/or "substantially" are/is utilized to describe a value, this is meant to encompass minor variations (up to +/−10%) from the stated value.

While several examples have been described in detail, it is to be understood that the disclosed examples may be modified. Therefore, the foregoing description is to be considered non-limiting.

While certain examples have been described, these examples have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure.

Features, materials, characteristics, or groups described in conjunction with a particular aspect, or example are to be understood to be applicable to any other aspect or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing examples. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some examples, the actual steps taken in the processes illustrated and/or disclosed may differ from those shown in the figures. Depending on the example, certain of the steps described above may be removed or others may be added. Furthermore, the features and attributes of the specific examples disclosed above may be combined in different ways to form additional examples, all of which fall within the scope of the present disclosure. Also, the separation of various system components in the implementations described above should not be understood as requiring such separation in all implementations, and it should be understood that the described components and systems can generally be integrated together in a single product or packaged into multiple products. For example, any of the components for an energy storage system described herein can be provided separately, or integrated together (e.g., packaged together, or attached together) to form an energy storage system.

For purposes of this disclosure, certain aspects, advantages, and novel features are described herein. Not necessarily all such advantages may be achieved in accordance with any particular example. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain examples include, while other examples do not include, certain features, elements, and/or steps. Thus, such conditional language is not generally intended to imply that features, elements, and/or steps are in any way required for one or more examples or that one or more examples necessarily include logic for deciding, with or without user input or prompting, whether these features, elements, and/or steps are included or are to be performed in any particular example.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain examples require the presence of at least one of X, at least one of Y, and at least one of Z.

Language of degree used herein, such as the terms "approximately," "about," "generally," and "substantially" represent a value, amount, or characteristic close to the stated value, amount, or characteristic that still performs a desired function or achieves a desired result.

The scope of the present disclosure is not intended to be limited by the specific disclosures of preferred examples in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A device, comprising:
   a middle well comprising a fluidic tunnel;
   a cis well associated with a cis electrode, wherein a first nanoscale opening is disposed between the cis well and the middle well;
   a trans well associated with a trans electrode, wherein a porous structure is disposed between the trans well and the middle well; and
   a field effect transistor (FET) positioned between the first nanoscale opening and the porous structure, the FET comprising:
      a source, a drain, and a channel connecting the source to the drain, wherein the channel comprises a gate oxide layer having an upper surface fluidically exposed to the middle well,
   wherein the middle well fluidically connects the cis well to the trans well, and wherein the fluidic tunnel does not extend through the channel.

2. The device as defined in claim 1, wherein the FET is a nanowire transistor.

3. The device as defined in claim 2, wherein the channel has a length along a direction from the source to the drain, a height along a direction from the cis electrode to the trans electrode, and a width along a direction at least substantially orthogonal to both the length and the height, and wherein the length is at least about 10 times the width or the height.

4. The device as defined in claim 3, wherein a boundary of the fluidic tunnel in a plane defined by the length and the width is disc shaped.

5. The device as defined in claim 1, wherein the FET is a nanosheet transistor.

6. The device as defined in claim 5, wherein the channel has a length along a direction from the source to the drain, a height along a direction from the cis electrode to the trans electrode, and a width along a direction at least partially orthogonal to both the length and the height, wherein the length is at least about 5 times the height, and wherein the width is at least about 5 times the height.

7. The device as defined in claim 6, wherein a boundary of the fluidic tunnel in a plane defined by the length and the width is oblong shaped.

8. The device as defined in claim 1, wherein the porous structure comprises a SiCOH film.

9. The device as defined in claim 1, further comprising a membrane positioned between the cis well and the middle well, wherein the first nanoscale opening extends through the membrane.

10. The device as defined in claim 1, wherein the gate oxide layer has a thickness between about 1 to about 10 nm.

11. The device as defined in claim 1, wherein the gate oxide layer has a thickness between about 2 and about 4 nm.

12. A device, comprising:
a middle well;
a cis well associated with a cis electrode, wherein a first nanoscale opening is disposed between the cis well and the middle well;
a trans well associated with a trans electrode, wherein a second nanoscale opening is disposed between the trans well and the middle well; and
a field effect transistor (FET) positioned between the first nanoscale opening and the second nanoscale opening, the FET comprising:
a source, a drain, and a channel connecting the source to the drain,
wherein the channel comprises a gate oxide layer operably connected to a metal structure,
wherein the gate oxide layer is not fluidically exposed,
wherein the middle well fluidically connects the cis well to the trans well, and
wherein the metal structure has at least one surface fluidically exposed to the middle well.

13. The device as defined in claim 12, wherein the at least one fluidically exposed surface of the metal structure is formed of a corrosion-resistant material.

14. The device as defined in claim 12, wherein the metal structure has at least one partially vertical surface, at least two partially vertical surfaces, at least one partially horizontal surface, at least two partially horizontal surfaces, or any combination thereof, fluidically exposed to the middle well, wherein a vertical direction is a direction from the cis electrode to the trans electrode, and wherein a horizontal direction is orthogonal to the vertical direction.

15. The device as defined in claim 12, wherein the metal structure has at least one cup-shaped substructure fluidically exposed to the middle well.

16. The device as defined in claim 12, wherein a portion of the metal structure fluidically exposed to the middle well comprises at least one hole or opening.

17. The device as defined in claim 12, wherein a portion of the metal structure fluidically exposed to the middle well comprises at least two holes or openings.

18. A device, comprising:
a middle well comprising a fluidic tunnel;
a cis well associated with a cis electrode, wherein a first nanoscale opening is disposed between the cis well and the middle well;
a trans well associated with a trans electrode, wherein a second nanoscale opening is disposed between the trans well and the middle well; and
a field effect transistor (FET) positioned between the first nanoscale opening and the second nanoscale opening, the FET comprising:
a source, a drain, and a channel connecting the source to the drain,
wherein the channel comprises a gate oxide layer having an upper surface fluidically exposed to the middle well,
wherein the middle well fluidically connects the cis well to the trans well,
wherein the fluidic tunnel does not extend through the channel,
wherein the gate oxide layer further comprises a lower surface fluidically exposed to the middle well.

19. The device as defined in claim 18, wherein the FET is a nanowire transistor.

20. The device as defined in claim 19, wherein the channel has a length along a direction from the source to the drain, a height along a direction from the cis electrode to the trans electrode, and a width along a direction at least substantially orthogonal to both the length and the height, and wherein the length is at least about 10 times the width or the height.

21. The device as defined in claim 20, wherein a boundary of the fluidic tunnel in a plane defined by the length and the width is disc shaped.

22. The device as defined in claim 18, wherein the FET is a nanosheet transistor.

23. The device as defined in claim 22, wherein the channel has a length along a direction from the source to the drain, a height along a direction from the cis electrode to the trans electrode, and a width along a direction at least partially orthogonal to both the length and the height, wherein the length is at least about 5 times the height, and wherein the width is at least about 5 times the height.

24. The device as defined in claim 23, wherein a boundary of the fluidic tunnel in a plane defined by the length and the width is oblong shaped.

25. The device as defined in claim 18, further comprising a membrane positioned between the cis well and the middle well, wherein the first nanoscale opening extends through the membrane.

26. The device as defined in claim 18, wherein the gate oxide layer has a thickness between about 1 to about 10 nm.

27. The device as defined in claim 18, wherein the gate oxide layer has a thickness between about 2 and about 4 nm.

28. The device as defined in claim 18, wherein the device comprises a nanopore sequencer.

* * * * *